United States Patent
Ropo et al.

(10) Patent No.: US 12,064,645 B2
(45) Date of Patent: Aug. 20, 2024

(54) METHODS AND SYSTEMS USED FOR PLANNING RADIATION TREATMENT

(71) Applicant: Varian Medical Systems International AG., Cham (CH)

(72) Inventors: Matti Ropo, Helsinki (FI); Michiko Rossi, Espoo (FI); Pierre Lansonneur, Helsinki (FI); Viljo Petaja, Espoo (FI)

(73) Assignee: SIEMENS HEALTHINEERS INTERNATIONAL AG, Steinhausen (CH)

( * ) Notice: Subject to any disclaimer, the term of this patent is extended or adjusted under 35 U.S.C. 154(b) by 854 days.

(21) Appl. No.: 16/920,232

(22) Filed: Jul. 2, 2020

(65) Prior Publication Data

US 2022/0001206 A1 Jan. 6, 2022

(51) Int. Cl.
*A61N 5/10* (2006.01)

(52) U.S. Cl.
CPC .................. *A61N 5/1031* (2013.01)

(58) Field of Classification Search
CPC ............ A61N 2005/1087; A61N 5/103; A61N 5/1081; A61N 5/1031; A61N 5/1045
See application file for complete search history.

(56) References Cited

U.S. PATENT DOCUMENTS

| | | |
|---|---|---|
| 4,163,901 A | 8/1979 | Azam |
| 4,914,681 A | 4/1990 | Klingenbeck et al. |
| 5,153,900 A | 10/1992 | Nomikos et al. |
| 5,267,294 A | 11/1993 | Kuroda |
| 5,550,378 A | 8/1996 | Skillicorn et al. |
| 5,610,967 A | 3/1997 | Moorman et al. |
| 5,625,663 A | 4/1997 | Swerdloff et al. |
| 5,682,412 A | 10/1997 | Skillicom et al. |
| 5,757,885 A | 5/1998 | Yao et al. |
| 6,198,802 B1 | 3/2001 | Elliott et al. |
| 6,222,544 B1 | 4/2001 | Tarr et al. |
| 6,234,671 B1 | 5/2001 | Solomon et al. |
| 6,260,005 B1 | 7/2001 | Yang et al. |
| 6,379,380 B1 | 4/2002 | Satz |

(Continued)

FOREIGN PATENT DOCUMENTS

| | | |
|---|---|---|
| CN | 104001270 | 8/2014 |
| CN | 106730407 | 5/2017 |

(Continued)

OTHER PUBLICATIONS https://www.bnl.gov/nsrl/userguide/bragg-curves-and-peaks.php; accessed in 2015 by Wayback Machine (https://web.archive.org/) (Year: 2015).*

(Continued)

*Primary Examiner* — Christine H Matthews
(74) *Attorney, Agent, or Firm* — Harness, Dickey & Pierce, P.L.C.

(57) ABSTRACT

Computer-implemented methods for planning radiation treatment are used to identify, for a given isocenter and given beam energy, beam delivery angles where beam fields satisfy a criterion for transmission fields (fields with a Bragg peak that is significantly or entirely outside of a patient's body). Those beam angles can be determined and evaluated before dose calculations are performed. Treatment planning can be performed using selected, satisfactory beam angles.

19 Claims, 10 Drawing Sheets

(56) References Cited

U.S. PATENT DOCUMENTS

| | | |
|---|---|---|
| 6,411,675 B1 | 6/2002 | Llacer |
| 6,445,766 B1 | 9/2002 | Whitham |
| 6,504,899 B2 | 1/2003 | Pugachev et al. |
| 6,580,940 B2 | 6/2003 | Gutman |
| 6,993,112 B2 | 1/2006 | Hesse |
| 7,268,358 B2 | 9/2007 | Ma et al. |
| 7,453,983 B2 | 11/2008 | Schildkraut et al. |
| 7,515,681 B2 | 4/2009 | Ebstein |
| 7,522,706 B2 | 4/2009 | Lu et al. |
| 7,560,715 B2 | 7/2009 | Pedroni |
| 7,590,219 B2 | 9/2009 | Maurer, Jr. et al. |
| 7,616,735 B2 | 11/2009 | Maciunas et al. |
| 7,623,623 B2 | 11/2009 | Raanes et al. |
| 7,778,691 B2 | 8/2010 | Zhang et al. |
| 7,807,982 B2 | 10/2010 | Nishiuchi et al. |
| 7,831,289 B2 | 11/2010 | Riker et al. |
| 7,835,492 B1 | 11/2010 | Sahadevan |
| 7,907,699 B2 | 3/2011 | Long et al. |
| 8,284,898 B2 | 10/2012 | Ho et al. |
| 8,306,184 B2 | 11/2012 | Chang et al. |
| 8,401,148 B2 | 3/2013 | Lu et al. |
| 8,406,844 B2 | 3/2013 | Ruchala et al. |
| 8,559,596 B2 | 10/2013 | Thomson et al. |
| 8,600,003 B2 | 12/2013 | Zhou et al. |
| 8,613,694 B2 | 12/2013 | Walsh |
| 8,636,636 B2 | 1/2014 | Shukla et al. |
| 8,644,571 B1 | 2/2014 | Schulte et al. |
| 8,716,663 B2 | 5/2014 | Brusasco et al. |
| 8,836,332 B2 | 9/2014 | Shvartsman et al. |
| 8,847,179 B2 | 9/2014 | Fujitaka et al. |
| 8,903,471 B2 | 12/2014 | Heid |
| 8,917,813 B2 | 12/2014 | Maurer, Jr. |
| 8,948,341 B2 | 2/2015 | Beckman |
| 8,958,864 B2 | 2/2015 | Amies et al. |
| 8,983,573 B2 | 3/2015 | Carlone et al. |
| 8,986,186 B2 | 3/2015 | Zhang et al. |
| 8,992,404 B2 | 3/2015 | Graf et al. |
| 8,995,608 B2 | 3/2015 | Zhou et al. |
| 9,018,603 B2 | 4/2015 | Loo et al. |
| 9,033,859 B2 | 5/2015 | Fieres et al. |
| 9,079,027 B2 | 7/2015 | Agano et al. |
| 9,149,656 B2 | 10/2015 | Tanabe |
| 9,155,908 B2 | 10/2015 | Meltsner et al. |
| 9,233,260 B2 | 1/2016 | Slatkin et al. |
| 9,258,876 B2 | 2/2016 | Cheung et al. |
| 9,283,406 B2 | 3/2016 | Prieels |
| 9,308,391 B2 | 4/2016 | Liu et al. |
| 9,330,879 B2 | 5/2016 | Lewellen et al. |
| 9,333,374 B2 | 5/2016 | Iwata |
| 9,468,777 B2 | 10/2016 | Fallone et al. |
| 9,517,358 B2 | 12/2016 | Velthuis et al. |
| 9,526,918 B2 | 12/2016 | Kruip |
| 9,545,444 B2 | 1/2017 | Strober et al. |
| 9,583,302 B2 | 2/2017 | Figueroa Saavedra et al. |
| 9,636,381 B2 | 5/2017 | Basile |
| 9,636,525 B1 | 5/2017 | Sahadevan |
| 9,649,298 B2 | 5/2017 | Djonov et al. |
| 9,656,098 B2 | 5/2017 | Goer |
| 9,694,204 B2 | 7/2017 | Hardemark |
| 9,776,017 B2 | 10/2017 | Flynn et al. |
| 9,786,054 B2 | 10/2017 | Taguchi et al. |
| 9,786,093 B2 | 10/2017 | Svensson |
| 9,786,465 B2 | 10/2017 | Li et al. |
| 9,795,806 B2 | 10/2017 | Matsuzaki et al. |
| 9,801,594 B2 | 10/2017 | Boyd et al. |
| 9,844,358 B2 | 12/2017 | Wiggers et al. |
| 9,854,662 B2 | 12/2017 | Mishin |
| 9,884,206 B2 | 2/2018 | Schulte et al. |
| 9,931,522 B2 | 4/2018 | Bharadwaj et al. |
| 9,962,562 B2 | 5/2018 | Fahrig et al. |
| 9,974,977 B2 | 5/2018 | Lachaine et al. |
| 9,987,502 B1 | 6/2018 | Gattiker et al. |
| 10,007,961 B2 | 6/2018 | Grudzinski et al. |
| 10,022,564 B2 | 7/2018 | Thieme et al. |
| 10,071,264 B2 | 9/2018 | Liger |
| 10,080,912 B2 | 9/2018 | Kwak et al. |
| 10,092,774 B1 | 10/2018 | Vanderstraten et al. |
| 10,183,179 B1 | 1/2019 | Smith et al. |
| 10,188,875 B2 | 1/2019 | Kwak et al. |
| 10,206,871 B2 | 2/2019 | Lin et al. |
| 10,212,800 B2 | 2/2019 | Agustsson et al. |
| 10,232,193 B2 | 3/2019 | Iseki |
| 10,258,810 B2 | 4/2019 | Zwart et al. |
| 10,272,264 B2 | 4/2019 | Ollila et al. |
| 10,279,196 B2 | 5/2019 | West et al. |
| 10,293,184 B2 | 5/2019 | Pishdad et al. |
| 10,307,614 B2 | 6/2019 | Schnarr |
| 10,307,615 B2 | 6/2019 | Ollila et al. |
| 10,315,047 B2 | 6/2019 | Glimelius et al. |
| 10,413,755 B1 | 9/2019 | Sahadevan |
| 10,449,389 B2 | 10/2019 | Ollila et al. |
| 10,485,988 B2 | 11/2019 | Kuusela et al. |
| 10,525,285 B1 | 1/2020 | Friedman |
| 10,549,117 B2 | 2/2020 | Vanderstraten et al. |
| 10,603,514 B2 | 3/2020 | Grittani et al. |
| 10,609,806 B2 | 3/2020 | Roecken et al. |
| 10,636,609 B1 | 4/2020 | Bertsche et al. |
| 10,660,588 B2 | 5/2020 | Boyd et al. |
| 10,661,100 B2 | 5/2020 | Shen |
| 10,682,528 B2 | 6/2020 | Ansorge et al. |
| 10,702,716 B2 | 7/2020 | Heese |
| 10,758,746 B2 | 9/2020 | Kwak et al. |
| 10,870,018 B2 | 12/2020 | Bartkoski et al. |
| 2007/0287878 A1 | 12/2007 | Fantini et al. |
| 2008/0023644 A1 | 1/2008 | Pedroni |
| 2009/0063110 A1 | 3/2009 | Failla et al. |
| 2009/0287467 A1 | 11/2009 | Sparks et al. |
| 2010/0119032 A1 | 5/2010 | Yan et al. |
| 2010/0177870 A1 | 7/2010 | Nord et al. |
| 2010/0178245 A1 | 7/2010 | Arnsdorf et al. |
| 2010/0260317 A1 | 10/2010 | Chang et al. |
| 2011/0006224 A1 | 1/2011 | Maltz et al. |
| 2011/0091015 A1 | 4/2011 | Yu et al. |
| 2011/0135058 A1 | 6/2011 | Sgouros et al. |
| 2012/0076271 A1 | 3/2012 | Yan et al. |
| 2012/0157746 A1 | 6/2012 | Meltsner et al. |
| 2012/0171745 A1 | 7/2012 | Itoh |
| 2012/0197058 A1 | 8/2012 | Shukla et al. |
| 2013/0116929 A1 | 5/2013 | Carlton et al. |
| 2013/0150922 A1 | 6/2013 | Butson et al. |
| 2013/0177641 A1 | 7/2013 | Ghoroghchian |
| 2013/0231516 A1 | 9/2013 | Loo et al. |
| 2014/0177807 A1 | 6/2014 | Lewellen et al. |
| 2014/0185776 A1 | 7/2014 | Li et al. |
| 2014/0206926 A1 | 7/2014 | van der Laarse |
| 2014/0275706 A1 | 9/2014 | Dean et al. |
| 2014/0369476 A1 | 12/2014 | Harding |
| 2015/0011817 A1 | 1/2015 | Feng |
| 2015/0202464 A1 | 7/2015 | Brand et al. |
| 2015/0306423 A1 | 10/2015 | Bharat et al. |
| 2016/0279444 A1 | 9/2016 | Schlosser |
| 2016/0310764 A1 | 10/2016 | Bharadwaj et al. |
| 2017/0189721 A1 | 7/2017 | Sumanaweera et al. |
| 2017/0203129 A1 | 7/2017 | Dessy |
| 2017/0281973 A1 | 10/2017 | Allen et al. |
| 2018/0015304 A1* | 1/2018 | Ohishi ................ A61N 5/1049 |
| 2018/0021594 A1 | 1/2018 | Papp et al. |
| 2018/0043183 A1 | 2/2018 | Sheng et al. |
| 2018/0056090 A1 | 3/2018 | Jordan et al. |
| 2018/0099154 A1 | 4/2018 | Prieels |
| 2018/0099155 A1 | 4/2018 | Prieels et al. |
| 2018/0099159 A1 | 4/2018 | Forton et al. |
| 2018/0154183 A1 | 6/2018 | Sahadevan |
| 2018/0197303 A1 | 7/2018 | Jordan et al. |
| 2018/0207425 A1 | 7/2018 | Carlton et al. |
| 2018/0236268 A1 | 8/2018 | Zwart et al. |
| 2019/0022407 A1 | 1/2019 | Abel et al. |
| 2019/0022409 A1* | 1/2019 | Vanderstraten ...... A61N 5/1081 |
| 2019/0022422 A1 | 1/2019 | Trail et al. |
| 2019/0046813 A1* | 2/2019 | Zhou ...................... A61N 5/10 |
| 2019/0054315 A1 | 2/2019 | Isola et al. |
| 2019/0070435 A1 | 3/2019 | Joe Anto et al. |
| 2019/0168027 A1 | 6/2019 | Smith et al. |
| 2019/0255361 A1 | 8/2019 | Mansfield |

(56) References Cited

U.S. PATENT DOCUMENTS

| | | |
|---|---|---|
| 2019/0299027 A1 | 10/2019 | Fujii et al. |
| 2019/0299029 A1 | 10/2019 | Inoue |
| 2019/0351259 A1 | 11/2019 | Lee et al. |
| 2020/0001118 A1 | 1/2020 | Snider, III et al. |
| 2020/0022248 A1 | 1/2020 | Yi et al. |
| 2020/0030633 A1 | 1/2020 | Van Heteren et al. |
| 2020/0035438 A1 | 1/2020 | Star-Lack et al. |
| 2020/0069818 A1 | 3/2020 | Jaskula-Ranga et al. |
| 2020/0105395 A1 | 4/2020 | Huth et al. |
| 2020/0164224 A1 | 5/2020 | Vanderstraten et al. |
| 2020/0178890 A1 | 6/2020 | Otto |
| 2020/0197730 A1 | 6/2020 | Safavi-Naeini et al. |
| 2020/0254279 A1 | 8/2020 | Ohishi |
| 2020/0269068 A1 | 8/2020 | Abel et al. |
| 2020/0276456 A1 | 9/2020 | Swerdloff |
| 2020/0282234 A1 | 9/2020 | Folkerts et al. |

FOREIGN PATENT DOCUMENTS

| | | |
|---|---|---|
| CN | 107362464 | 11/2017 |
| CN | 109966662 | 7/2019 |
| CN | 111481840 | 8/2020 |
| CN | 111481841 | 8/2020 |
| EA | 010207 | 6/2008 |
| EP | 0979656 | 2/2000 |
| EP | 2759317 | 7/2014 |
| EP | 3338858 | 6/2018 |
| EP | 3384961 | 10/2018 |
| EP | 3421087 | 1/2019 |
| EP | 3453427 | 3/2019 |
| EP | 3586920 | 1/2020 |
| JP | 2617283 | 6/1997 |
| JP | 2019097969 | 6/2019 |
| JP | 2020081424 A | 6/2020 |
| WO | 2007017177 | 2/2007 |
| WO | 2010018476 | 2/2010 |
| WO | 2013081218 | 6/2013 |
| WO | 2013133936 | 9/2013 |
| WO | 2014139493 | 9/2014 |
| WO | 2015038832 | 3/2015 |
| WO | 2015102680 | 7/2015 |
| WO | 2016122957 | 8/2016 |
| WO | 2017156316 | 9/2017 |
| WO | 2017174643 | 10/2017 |
| WO | 2018137772 | 8/2018 |
| WO | 2018152302 | 8/2018 |
| WO | 2019097250 | 5/2019 |
| WO | 2019103983 | 5/2019 |
| WO | 2019164835 | 8/2019 |
| WO | 2019166702 | 9/2019 |
| WO | 2019173823 | 9/2019 |
| WO | 2019185378 | 10/2019 |
| WO | 2019222436 | 11/2019 |
| WO | 2020018904 | 1/2020 |
| WO | 2020064832 | 4/2020 |
| WO | 2020107121 | 6/2020 |
| WO | 2020159360 | 8/2020 |

OTHER PUBLICATIONS

M. McManus et al., "The challenge of ionisation chamber dosimetry in ultra-short pulsed high dose-rate Very High Energy Electron beams," Sci Rep 10, 9089 (2020), published Jun. 3, 2020, https://doi.org/10.1038/s41598-020-65819-y.

Ibrahim Oraiqat et al., "An Ionizing Radiation Acoustic Imaging (iRAI) Technique for Real-Time Dosimetric Measurements for Flash Radiotherapy," Medical Physics, vol. 47, Issue 10, Oct. 2020, pp. 5090-5101, First published: Jun. 27, 2020, https://doi.org/10.1002/mp.14358.

K. Petersson et al., "Dosimetry of ultra high dose rate irradiation for studies on the biological effect induced in normal brain and GBM," ICTR-PHE 2016, p. S84, Feb. 2016, https://publisher-connector.core.ac.uk/resourcesync/data/elsevier/pdf/14c/aHR0cDovL2FwaS5 lbHNIdmllci5jb20vY29udGVudC9hcnRpY2xlL3BpaS9zMDE2Nz gxNDAxNjMwMTcyNA==.pdf.

Susanne Auer et al., "Survival of tumor cells after proton irradiation with ultra-high dose rates," Radiation Oncology 2011, 6:139, Published Oct. 18, 2011, DOI: https://doi.org/10.1186/1748-717X-6-139.

Cynthia E. Keen, "Clinical linear accelerator delivers Flash radiotherapy," Physics World, Apr. 23, 2019, IOP Publishing Ltd, https://physicsworld.com/a/clinical-linear-accelerator-delivers-flash-radiotherapy/.

Fan et al., "Emission guided radiation therapy for lung and prostate cancers: A feasibility study on a digital patient," Med Phys. Nov. 2012; 39(11): 7140-7152. Published online Nov. 5, 2012. https://www.ncbi.nlm.nih.gov/pmc/articles/PMC3505203/ doi: 10.1118/1.4761951.

Favaudon et al., "Ultrahigh dose-rate, "flash" irradiation minimizes the side-effects of radiotherapy," Cancer / Radiotherapy, vol. 19, Issues 6-7 , Oct. 2015 , pp. 526-531, Available online Aug. 12, 2015, https://doi.org/10.1016/j.canrad.2015.04.006.

O. Zlobinskaya et al., "The Effects of Ultra-High Dose Rate Proton Irradiation on Growth Delay in the Treatment of Human Tumor Xenografts in Nude Mice," Radiation Research, 181(2):177-183. Published Feb. 13, 2014, DOI: http://dx.doi.org/10.1667/RR13464.1.

Bjorn Zackrisson, "Biological Effects Of High Energy Radiation And Ultra High Dose Rates," Umea University Medical Dissertations, New series No. 315—ISSN 0346-6612, From the Department of Oncology, University of Umea, Umea, Sweden, ISBN 91-7174-614-5, Printed in Sweden by the Printing Office of Umea University, Umea, 1991.

P. Montay-Gruel et al., "Irradiation in a flash: Unique sparing of memory in mice after whole brain irradiation with dose rates above 100 Gy/s," Radiotherapy and Oncology, vol. 124, Issue 3, Sep. 2017, pp. 365-369, Available online May 22, 2017, doi: 10.1016/j.radonc.2017.05.003.

Bw Loo et al., "Delivery of Ultra-Rapid Flash Radiation Therapy and Demonstration of Normal Tissue Sparing After Abdominal Irradiation of Mice," International Journal of Radiation Oncology, Biology, Physics, vol. 98, Issue 2, p. E16, Supplement: S Meeting Abstract: P003, Published: Jun. 1, 2017, DOI: https://doi.org/10.1016/j.ijrobp.2017.02.101.

Bhanu Prasad Venkatesulu et al., "Ultra high dose rate (35 Gy/sec) radiation does not spare the normal tissue in cardiac and splenic models of lymphopenia and gastrointestinal syndrome," Sci Rep 9, 17180 (2019), Published Nov. 20, 2019, DOI: https://doi.org/10.1038/s41598-019-53562-y.

P. Montay-Gruel et al., "Long-term neurocognitive benefits of Flash radiotherapy driven by reduced reactive oxygen species," PNAS May 28, 2019, vol. 116, No. 22, pp. 10943-10951; first published May 16, 2019, https://doi.org/10.1073/pnas.1901777116.

Peter G. Maxim et al., "Flash radiotherapy: Newsflash or flash in the pan?", Medical Physics, 46 (10), Oct. 2019, pp. 4287-4290, American Association of Physicists in Medicine, First published: Jun. 27, 2019, https://doi.org/10.1002/mp.13685.

Andrei Pugachev et al., "Pseudo beam's-eye-view as applied to beam orientation selection in intensity-modulated radiation therapy," Int. J. Radiation Oncology Biol. Phys., vol. 51, Issue 5, P1361-1370, Dec. 1, 2001, DOI: https://doi.org/10.1016/S0360-3016(01)01736-9.

Xiaodong Zhang et al., "Intensity-Modulated Proton Therapy Reduces the Dose to Normal Tissue Compared With Intensity-Modulated Radiation Therapy or Passive Scattering Proton Therapy and Enables Individualized Radical Radiotherapy for Extensive Stage IIIB Non-Small-Cell Lung Cancer: A Virtual Clinical Study," Int. J. Radiation Oncology Biol. Phys., vol. 77, No. 2, pp. 357-366, 2010, Available online Aug. 5, 2009, DOI: https://doi.org/10.1016/j.ijrobp.2009.04.028.

A. J. Lomax et al., "Intensity modulated proton therapy: A clinical example," Medical Physics, vol. 28, Issue 3, Mar. 2001, pp. 317-324, First published: Mar. 9, 2001, https://doi.org/10.1118/1.1350587.

(56) References Cited

OTHER PUBLICATIONS

Lamberto Widesott et al., "Intensity-Modulated Proton Therapy Versus Helical Tomotherapy in Nasopharynx Cancer: Planning Comparison and NTCP Evaluation," Int. J. Radiation Oncology Biol. Phys., vol. 72, No. 2, pp. 589-596, Oct. 1, 2008, Available online Sep. 13, 2008, DOI: https://doi.org/10.1016/j.ijrobp.2008.05.065.

Andrei Pugachev et al., "Role of beam orientation optimization in intensity-modulated radiation therapy," Int. J. Radiation Oncology Biol. Phys., vol. 50, No. 2, pp. 551-560, Jun. 1, 2001, Available online May 10, 2001, DOI: https://doi.org/10.1016/S0360-3016(01)01502-4.

Damien C. Weber et al., "Radiation therapy planning with photons and protons for early and advanced breast cancer: an overview," Radiat Oncol. 2006; 1: 22. Published online Jul. 20, 2006, doi: 10.1186/1748-717X-1-22.

RaySearch Laboratories, "Leading the way in cancer treatment, Annual Report 2013," RaySearch Laboratories (publ), Stockholm, Sweden, 94 pages, Apr. 2014, https://www.raysearchlabs.com/siteassets/about-overview/media-center/wp-re-ev-n-pdfs/brochures/raysearch-ar-2013-eng.pdf.

Fredrik Carlsson, "Utilizing Problem Structure in Optimization of Radiation Therapy," KTH Engineering Sciences, Doctoral Thesis, Stockholm, Sweden, Apr. 2008, Optimization and Systems Theory, Department of Mathematics, Royal Institute of Technology, Stockholm, Sweden, ISSN 1401-2294, https://www.raysearchlabs.com/globalassets/about-overview/media-center/wp-re-ev-n-pdfs/publications/thesis-fredrik_light.pdf.

Chang-Ming Charlie Ma, "Physics and Dosimetric Principles of SRS and SBRT," Mathews J Cancer Sci. 4(2): 22, 2019, published: Dec. 11, 2019, ISSN: 2474-6797, DOI: https://doi.org/10.30654/MJCS.10022.

Alterego-admin, "Conventional Radiation Therapy May Not Protect Healthy Brain Cells," International Neuropsychiatric Association—INA, Oct. 10, 2019, https://inawebsite.org/conventional-radiation-therapy-may-not-protect-healthy-brain-cells/.

Aafke Christine Kraan, "Range verification methods in particle therapy: underlying physics and Monte Carlo modeling," Frontiers in Oncology, Jul. 7, 2015, vol. 5, Article 150, 27 pages, doi: 10.3389/fonc.2015.00150.

Wayne D. Newhauser et al., "The physics of proton therapy," Physics in Medicine & Biology, Mar. 24, 2015, 60 R155-R209, Institute of Physics and Engineering in Medicine, IOP Publishing, doi: 10.1088/0031-9155/60/8/R155.

S E McGowan et al., "Treatment planning optimisation in proton therapy," Br J Radiol, 2013, 86, 20120288, The British Institute of Radiology, 12 pages, DOI: 10.1259.bjr.20120288.

Steven Van De Water et al., "Towards Flash proton therapy: the impact of treatment planning and machine characteristics on achievable dose rates," Acta Oncologica, Jun. 26, 2019, vol. 58, No. 10, p. 1462-1469, Taylor & Francis Group, DOI: 10.1080/0284186X.2019.1627416.

J. Groen, "Flash optimisation in clinical IMPT treatment planning," MSc Thesis, Jul. 1, 2020, Erasmus University Medical Center, department of radiotherapy, Delft University of Technology, 72 pages.

Muhammad Ramish Ashraf et al., "Dosimetry for Flash Radiotherapy: A Review of Tools and the Role of Radioluminescence and Cherenkov Emission," Frontiers in Oncology, Aug. 21, 2020, vol. 8, Article 328, 20 pages, doi: 10.3389/fphy.2020.00328.

Emil Schuler et al., "Experimental Platform for Ultra-high Dose Rate Flash Irradiation of Small Animals Using a Clinical Linear Accelerator," International Journal of Radiation Oncology, Biology, Physics, vol. 97, No. 1, Sep. 2016, pp. 195-203.

Elette Engels et al., "Toward personalized synchrotron microbeam radiation therapy," Scientific Reports, 10:8833, Jun. 1, 2020, 13 pages, DOI: https://doi.org/10.1038/s41598-020-65729-z.

P-H Mackeprang et al., "Assessing dose rate distributions in VMAT plans" (Accepted Version), Accepted Version: https://boris.unibe.ch/92814/8/dose_rate_project_revised_submit.pdf Published Version: 2016, Physics in medicine and biology, 61(8), pp. 3208-3221. Institute of Physics Publishing IOP, published Mar. 29, 2016, https://boris.unibe.ch/92814/.

Xiaoying Liang et al., "Using Robust Optimization for Skin Flashing in Intensity Modulated Radiation Therapy for Breast Cancer Treatment: A Feasibility Study," Practical Radiation Oncology, vol. 10, Issue 1, p. 59-69, Published by Elsevier Inc., Oct. 15, 2019.

Alexei Trofimov et al., "Optimization of Beam Parameters and Treatment Planning for Intensity Modulated Proton Therapy," Technology in Cancer Research & Treatment, vol. 2, No. 5, Oct. 2003, p. 437-444, Adenine Press.

Vladimir Anferov, "Scan pattern optimization for uniform proton beam scanning," Medical Physics, vol. 36, Issue 8, Aug. 2009, pp. 3560-3567, First published: Jul. 2, 2009.

Ryosuke Kohno et al., "Development of Continuous Line Scanning System Prototype for Proton Beam Therapy," International Journal of Particle Therapy, Jul. 11, 2017, vol. 3, Issue 4, p. 429-438, DOI: 10.14338/IJPT-16-00017.1.

Wenbo Gu et al., "Integrated Beam Orientation and Scanning-Spot Optimization in Intensity Modulated Proton Therapy for Brain and Unilateral Head and Neck Tumors," Med Phys. Author manuscript; available in PMC Apr. 1, 2019. https://www.ncbi.nlm.nih.gov/pmc/articles/PMC5904040/ Published in final edited form as: Med Phys. Apr. 2018; 45(4): 1338-1350. Published online Mar. 1, 2018. doi: 10.1002/mp.12788 Accepted manuscript online: Feb. 2, 2018.

Paul Morel et al., "Spot weight adaptation for moving target in spot scanning proton therapy," Frontiers in Oncology, May 28, 2015, vol. 5, Article 119, 7 pages, doi: 10.3389/fonc.2015.00119.

Simeon Nill et al., "Inverse planning of intensity modulated proton therapy," Zeitschrift fur Medizinische Physik, vol. 14, Issue 1, 2004, pp. 35-40, https://doi.org/10.1078/0939-3889-00198.

A. Lomax, "Intensity modulation methods for proton radiotherapy," Physics in Medicine & Biology, Jan. 1999, vol. 44, No. 1, pp. 185-205, doi: 10.1088/0031-9155/44/1/014.

M Kramer et al., "Treatment planning for heavy-ion radiotherapy: physical beam model and dose optimization," Physics in Medicine & Biology, 2000, vol. 45, No. 11, pp. 3299-3317, doi: 10.1088/0031-9155/45/11/313.

Harald Paganetti, "Proton Beam Therapy," Jan. 2017, Physics World Discovery, IOP Publishing Ltd, Bristol, UK, 34 pages, DOI: 10.1088/978-0-7503-1370-4.

Shinichi Shimizu et al., "A Proton Beam Therapy System Dedicated to Spot-Scanning Increases Accuracy with Moving Tumors by Real-Time Imaging and Gating and Reduces Equipment Size," PLoS One, Apr. 18, 2014, vol. 9, Issue 4, e94971, https://doi.org/10.1371/journal.pone.0094971.

Heng Li et al., "Reducing Dose Uncertainty for Spot-Scanning Proton Beam Therapy of Moving Tumors by Optimizing the Spot Delivery Sequence," International Journal of Radiation Oncology, Biology, Physics, vol. 93, Issue 3, Nov. 1, 2015, pp. 547-556, available online Jun. 18, 2015, https://doi.org/10.1016/j.ijrobp.2015.06.019.

Ion Beam Applications SA, "Netherlands Proton Therapy Center Delivers First Clinical Flash Irradiation," Imaging Technology News, May 2, 2019, Wainscot Media, https://www.itnonline.com/content/netherlands-proton-therapy-center-delivers-first-clinical-flash-irradiation.

R. M. De Kruijff, "Flash radiotherapy: ultra-high dose rates to spare healthy tissue," International Journal of Radiation Biology, 2020, vol. 96, No. 4, pp. 419-423, published online: Dec. 19, 2019, https://doi.org/10.1080/09553002.2020.1704912.

Mevion Medical Systems, "Focus On The Future: Flash Therapy," Press Releases, Sep. 16, 2019, https://www.mevion.com/newsroom/press-releases/focus-future-flash-therapy.

Joseph D. Wilson et al., "Ultra-High Dose Rate (Flash) Radiotherapy: Silver Bullet or Fool's Gold?", Frontiers in Oncology, Jan. 17, 2020, vol. 9, Article 1563, 12 pages, doi: 10.3389/fonc.2019.01563.

David P. Gierga, "Is Flash Radiotherapy coming?", International Organization for Medical Physics, 2020, https://www.iomp.org/iomp-news2-flash-radiotherapy/.

Abdullah Muhammad Zakaria et al., "Ultra-High Dose-Rate, Pulsed (Flash) Radiotherapy with Carbon Ions: Generation of Early, Tran-

(56) References Cited

OTHER PUBLICATIONS sient, Highly Oxygenated Conditions in the Tumor Environment," Radiation Research, Dec. 1, 2020, vol. 194, Issue 6, pp. 587-593, Radiation Research Society, Published: Aug. 27, 2020, doi: https://doi.org/10.1667/RADE-19-00015.1.

Yusuke Demizu et al., "Carbon Ion Therapy for Early-Stage Non-Small-Cell Lung Cancer," BioMed Research International, vol. 2014, Article ID 727962, 9 pages, Hindawi Publishing Corporation, published: Sep. 11, 2014, https://doi.org/10.1155/2014/727962.

Ivana Dokic et al., "Next generation multi-scale biophysical characterization of high precision cancer particle radiotherapy using clinical proton, helium-, carbon- and oxygen ion beams," Oncotarget, Aug. 30, 2016, vol. 7, No. 35, pp. 56676-56689, published online: Aug. 1, 2016, doi: 10.18632/oncotarget.10996.

Aetna Inc., "Proton Beam, Neutron Beam, and Carbon Ion Radiotherapy," 2020, No. 0270, http://www.aetna.com/cpb/medical/data/200_299/0270.html.

Nicholas W. Colangelo et al., "The Importance and Clinical Implications of Flash Ultra-High Dose-Rate Studies for Proton and Heavy Ion Radiotherapy," Radiat Res. Author manuscript; available in PMC Jan. 1, 2021. https://www.ncbi.nlm.nih.gov/pmc/articles/PMC6949397/ Published in final edited form as: Radiat Res. Jan. 2020; 193(1): 1-4. Published online Oct. 28, 2019. doi: 10.1667/RR15537.1.

Mncent Favaudon et al., "Ultrahigh dose-rate Flash irradiation increases the differential response between normal and tumor tissue in mice," Science Translational Medicine, Jul. 16, 2014, vol. 6, Issue 245, 245ra93, American Association for the Advancement of Science, DOI: 10.1126/scitranslmed.3008973.

"FlashRad: Ultra-high dose-rate Flash radiotherapy to minimize the complications of radiotherapy," 2014, https://siric.curie.fr/sites/default/files/atoms/files/flashrad.pdf.

Tami Freeman, "Flash radiotherapy: from preclinical promise to the first human treatment," Physics World, Aug. 6, 2019, IOP Publishing Ltd, https://physicsworld.com/a/flash-radiotherapy-from-preclinical-promise-to-the-first-human-treatment/.

Intraop Medical, Inc., "IntraOp and Lausanne University Hospital Announce Collaboration in Flash radiotherapy," Jun. 18, 2020, https://intraop.com/news-events/lausanne-university-flash-radiotherapy-collaboration/.

M.-C. Vozenin et al., "Biological Benefits of Ultra-high Dose Rate Flash Radiotherapy: Sleeping Beauty Awoken," Clin Oncol (R Coll Radiol). Author manuscript; available in PMC Nov. 12, 2019. https://www.ncbi.nlm.nih.gov/pmc/articles/PMC6850216/ Published in final edited form as: Clin Oncol (R Coll Radiol). Jul. 2019; 31(7): 407-415. Published online Apr. 19, 2019. doi: 10.1016/j.clon.2019.04.001.

Efstathios Kamperis et al., "A Flash back to radiotherapy's past and then fast forward to the future," J Cancer Prev Curr Res. 2019;10(6):142-144. published Nov. 13, 2019, DOI: 10.15406/jcpcr.2019.10.00407.

P. Symonds et al., "Flash Radiotherapy: The Next Technological Advance in Radiation Therapy?", Clinical Oncology, vol. 31, Issue 7, p. 405-406, Jul. 1, 2019, The Royal College of Radiologists, Published by Elsevier Ltd., DOI: https://doi.org/10.1016/j.clon.2019.05.011.

Swati Girdhani et al., "Abstract LB-280: Flash: A novel paradigm changing tumor irradiation platform that enhances therapeutic ratio by reducing normal tissue toxicity and activating immune pathways," Proceedings: AACR Annual Meeting 2019; Mar. 29-Apr. 3, 2019; Atlanta, GA, published Jul. 2019, vol. 79, Issue 13 Supplement, pp. LB-280, American Association for Cancer Research, DOI: https://doi.org/10.1158/1538-7445.AM2019-LB-280.

Bazalova-Carter et al., "On the capabilities of conventional x-ray tubes to deliver ultra-high (Flash) dose rates," Med. Phys. Dec. 2019; 46 (12):5690-5695, published Oct. 23, 2019, American Association of Physicists in Medicine, doi: 10.1002/mp. 13858. Epub Oct. 23, 2019. PMID: 31600830.

Manuela Buonanno et al., "Biological effects in normal cells exposed to Flash dose rate protons," Radiother Oncol. Author manuscript; available in PMC Oct. 1, 2020. https://www.ncbi.nlm.nih.gov/pmc/articles/PMC6728238/ Published in final edited form as: Radiother Oncol. Oct. 2019; 139: 51-55. Published online Mar. 5, 2019. doi: 10.1016/j.radonc.2019.02.009.

N. Rama et al., "Improved Tumor Control Through T-cell Infiltration Modulated by Ultra-High Dose Rate Proton Flash Using a Clinical Pencil Beam Scanning Proton System," International Journal of Radiation Oncology, Biology, Physics, vol. 105, Issue 1, Supplement , S164-S165, Sep. 1, 2019, Mini Oral Sessions, DOI: https://doi.org/10.1016/j.ijrobp.2019.06.187.

Inserm Press Office, "Radiotherapy 'flashes' to reduce side effects," Press Release, Jul. 16, 2014, https://presse.inserm.fr/en/radiotherapy-flashes-to-reduce-side-effects/13394/.

Eric S. Diffenderfer et al., "Design, Implementation, and in Vivo Validation of a Novel Proton Flash Radiation Therapy System," International Journal of Radiation Oncology, Biology, Physics, vol. 106, Issue 2, Feb. 1, 2020, pp. 440-448, Available online Jan. 9, 2020, Published by Elsevier Inc., DOI: https://doi.org/10.1016/j.ijrobp.2019.10.049.

Valerie Devillaine, "Radiotherapy and Radiation Biology," Institut Curie, Apr. 21, 2017, https://institut-curie.org/page/radiotherapy-and-radiation-biology.

Imaging Technology News, "ProNova and medPhoton to Offer Next Generation Beam Delivery, Advanced Imaging for Proton Therapy," Oct. 6, 2014, Wainscot Media, Link: https://www.itnonline.com/content/pronova-and-medphoton-offer-next-generation-beam-delivery-advanced-imaging-proton-therapy.

Oncolink Team, "Radiation Therapy: Which type is right for me?", OncoLink Penn Medicine, last reviewed Mar. 3, 2020, Trustees of the University of Pennsylvania, https://www.oncolink.org/cancer-treatment/radiation/introduction-to-radiation-therapy/radiation-therapy-which-type-is-right-for-me.

Marco Durante et al., "Faster and safer? Flash ultra-high dose rate in radiotherapy," Br J Radiol 2018; 91(1082): 20170628, British Institute of Radiology, Published Online: Dec. 15, 2017, https://doi.org/10.1259/bjr.20170628.

John R. Fischer, "PMB launches Flash radiotherapy system for use in clinical trials," HealthCare Business News, Jun. 29, 2020, DOTmed.com, Inc., https://www.dotmed.com/news/story/51662.

Marie-Catherine Vozenin et al., "The advantage of Flash radiotherapy confirmed in mini-pig and cat-cancer patients," Clinical Cancer Research, Author Manuscript Published OnlineFirst Jun. 6, 2018, https://clincancerres.aacrjournals.org/content/clincanres/early/2018/06/06/1078-0432.CCR-17-3375.full.pdf.

\* cited by examiner

METHODS AND SYSTEMS USED FOR PLANNING RADIATION TREATMENT

BACKGROUND

The use of radiation therapy to treat cancer is well known. Typically, radiation therapy involves directing a beam of high energy proton, photon, ion, or electron radiation ("therapeutic radiation") into a target or volume in a treatment target (e.g., a volume that includes a tumor or lesion).

Before a patient is treated with radiation, a treatment plan specific to that patient is developed. The plan defines various aspects of the therapy using simulations and optimizations that may be based on past experiences. In general, the purpose of the treatment plan is to deliver sufficient radiation to the unhealthy tissue while minimizing exposure of surrounding healthy tissue to the radiation.

The planner's goal is to find a solution that is optimal with respect to multiple clinical goals that may be contradictory in the sense that an improvement toward one goal may have a detrimental effect on reaching another goal. For example, a treatment plan that spares the liver from receiving a dose of radiation may result in the stomach receiving too much radiation. These types of tradeoffs lead to an iterative process in which the planner creates different plans to find the one plan that is best suited to achieving the desired outcome.

A relatively recent radiobiology study has demonstrated the effectiveness of delivering a relatively high therapeutic radiation dose to a target within a single, short period of time. This type of treatment is referred to generally herein as FLASH radiation therapy (FLASH RT). Evidence to date suggests that FLASH RT advantageously spares normal, healthy tissue from damage when that tissue is exposed to a high radiation dose for only a very short period of time.

Radiation therapy using proton beams has a significant advantage relative to the use of other types of beams. A proton beam reaches a depth in tissue that depends on the energy of the beam, and releases most of its energy (delivers most of its dose) at that depth. The region of a depth-dose curve where most of the energy is released is referred to as the Bragg peak of the beam. In certain circumstances, it is desirable to deliver a proton beam with a Bragg peak that is outside of the patient's body. However, the location of the Bragg peak depends on factors such as beam energy and patient geometry. For a beam of given energy, one beam field may have a Bragg peak that is outside the patient's body when the beam is delivered at one angle, but another beam field may have a Bragg peak that is inside the body when the beam is delivered at a different angle. A beam field with a Bragg peak outside the body may be referred to as a transmission field.

SUMMARY

Embodiments according to the present invention provide an improved method that can be used for generating and evaluating radiation treatment plans for radiation therapy including FLASH radiation therapy (FLASH RT).

Computer-implemented methods for planning radiation treatment in embodiments according to the invention are used to identify, for a given isocenter and given beam energy, beam delivery angles where the beam fields satisfy a criterion for transmission fields: the Bragg peak is partially, majorly, or entirely outside of a patient's body. Those beam angles can be determined and evaluated before dose calculations are performed. Consequently, treatment planning can be performed more efficiently by eliminating or avoiding beam angles that have a radiological thickness that is too large to satisfy the transmission field criterion (e.g., that would place the Bragg peak inside the body). Radiological thickness may be expressed as a water-equivalent distance or thickness or ratio.

More specifically, in embodiments of a computer-implemented method, information that defines a location of an isocenter that is based on the location of a treatment target is accessed (e.g., from computer system memory), a value of beam energy for a beam of radiation is accessed (e.g., from computer system memory), and a value of an angle of the beam relative to the treatment target is accessed (e.g., from computer system memory). In embodiments, the range (depth) of the beam, including the location of the Bragg peak, relative to the treatment target is determined using a radiological thickness for the location of the treatment target, without having to calculate a dose. Thus, the location of the Bragg peak for each beam field is readily determined, to also determine which beam fields (and which beam angles) satisfy the transmission field criterion.

In embodiments, a graphical user interface (GUI) that includes a rendering of the treatment target, and also includes a rendering of a field of the beam relative to the treatment target, is displayed. In such embodiments, the rendering of the field of the beam in the GUI indicates a location in the field of the Bragg peak. In embodiments, the rendering of the field of the beam in the GUI shows the range (depth) and coverage of the field relative to the treatment target. In embodiments, the rendering of the field of the beam shows the width (lateral size) of the field. The beam field rendered in the GUI can be moved to different positions (different angles) and the rendered range of the beam field is changed accordingly, to account for changes in the type of tissue that the beam field encounters when the angle is changed. Thus, the GUI allows a user to readily determine the location of the Bragg peak for each beam field, to determine which beam fields (and which beam angles) satisfy the transmission field criterion.

In embodiments, the transmission field criterion corresponds to an amount of the Bragg peak of the field that is outside a patient's body, and the criterion is satisfied when a threshold amount of the Bragg peak is outside the patient (e.g., all of, or X percent of, the Bragg peak is outside the body). When the criterion is satisfied, the value of the angle of the beam is included in a proposed or final radiation treatment plan.

Embodiments according to the invention allow a clinician to better evaluate and choose beam angles that place the Bragg peak partially (e.g., majorly) or entirely outside a patient's body. For example, in essentially a single glance at a GUI, a clinician can evaluate this aspect as well as other aspects of a proposed radiation treatment plan, make changes, and evaluate the results of the changes. Planning can be performed more efficiently because it is not necessary to calculate doses in order to evaluate a beam angle that might place a Bragg peak inside the patient's body.

In radiation therapy techniques in which the intensity of the particle beam is either constant or modulated across the field of delivery, such as in intensity modulated radiation therapy (IMRT) and intensity modulated particle therapy (IMPT), beam intensity is varied across each treatment region (volume in a treatment target) in a patient. Depending on the treatment modality, the degrees of freedom available for intensity modulation include, but are not limited to, beam shaping (collimation), beam weighting (spot scanning), and angle of incidence (which may be referred to as beam geometry). These degrees of freedom lead to an effectively infinite number of potential treatment plans, and therefore consistently and efficiently generating and evaluating high-quality treatment plans is beyond the capability of a human and relies on the use of a computer system, particularly considering the time constraints associated with the use of radiation therapy to treat ailments like cancer, as well as the large number of patients that are undergoing or need to undergo radiation therapy during any given time period.

Embodiments according to the invention improve radiation treatment planning and the treatment itself. Treatment plans generated as described herein are superior for sparing healthy tissue from radiation in comparison to conventional techniques for FLASH dose rates by optimizing the balance between the dose rate delivered to unhealthy tissue (e.g., a tumor) in a volume in a treatment target and the dose rate delivered to surrounding healthy tissue. When used with FLASH dose rates, management of patient motion is simplified because the doses are applied in a short period of time (e.g., less than a second). Treatment planning, while still a complex task, is improved relative to conventional treatment planning. In addition to these benefits, a GUI facilitates treatment planning by allowing a planner to readily visualize key elements of a proposed treatment plan, to readily visualize the effects of changes to the proposed plan and compare different plans, and to define and establish optimization objectives.

In summary, embodiments according to this disclosure pertain to generating and implementing a treatment plan that is the most effective (relative to other plans) and with the least (or most acceptable) side effects (e.g., a lower dose rate outside of the region being treated). Thus, embodiments according to the invention improve the field of radiation treatment planning specifically and the field of radiation therapy in general. Embodiments according to the invention allow more effective treatment plans to be generated quickly. Also, embodiments according to the invention help improve the functioning of computers because, for example, by reducing the complexity of generating treatment plans by, for example, eliminating the need to perform certain dose calculations, fewer computational resources are needed and consumed, meaning also that computer resources are freed up to perform other tasks.

Embodiments according to the invention are not necessarily limited to radiation therapy techniques such as IMRT and IMPT.

These and other objects and advantages of embodiments according to the present invention will be recognized by one skilled in the art after having read the following detailed description, which are illustrated in the various drawing figures.

This summary is provided to introduce a selection of concepts that are further described below in the detailed description that follows. This summary is not intended to identify key features or essential features of the claimed subject matter, nor is it intended to be used to limit the scope of the claimed subject matter.

BRIEF DESCRIPTION OF DRAWINGS

The accompanying drawings, which are incorporated in and form a part of this specification and in which like numerals depict like elements, illustrate embodiments of the present disclosure and, together with the detailed description, serve to explain the principles of the disclosure.

DETAILED DESCRIPTION

Reference will now be made in detail to the various embodiments of the present disclosure, examples of which are illustrated in the accompanying drawings. While described in conjunction with these embodiments, it will be understood that they are not intended to limit the disclosure to these embodiments. On the contrary, the disclosure is intended to cover alternatives, modifications and equivalents, which may be included within the spirit and scope of the disclosure as defined by the appended claims. Furthermore, in the following detailed description of the present disclosure, numerous specific details are set forth in order to provide a thorough understanding of the present disclosure. However, it will be understood that the present disclosure may be practiced without these specific details. In other instances, well-known methods, procedures, components, and circuits have not been described in detail so as not to unnecessarily obscure aspects of the present disclosure.

Some portions of the detailed descriptions that follow are presented in terms of procedures, logic blocks, processing, and other symbolic representations of operations on data bits within a computer memory. These descriptions and representations are the means used by those skilled in the data processing arts to most effectively convey the substance of their work to others skilled in the art. In the present application, a procedure, logic block, process, or the like, is conceived to be a self-consistent sequence of steps or instructions leading to a desired result. The steps are those utilizing physical manipulations of physical quantities. Usually, although not necessarily, these quantities take the form of electrical or magnetic signals capable of being stored, transferred, combined, compared, and otherwise manipulated in a computer system. It has proven convenient at times, principally for reasons of common usage, to refer to these signals as transactions, bits, values, elements, symbols, characters, samples, pixels, or the like.

It should be borne in mind, however, that all of these and similar terms are to be associated with the appropriate physical quantities and are merely convenient labels applied to these quantities. Unless specifically stated otherwise as apparent from the following discussions, it is appreciated that throughout the present disclosure, discussions utilizing terms such as "accessing," "generating," "representing,"

Figure 1:
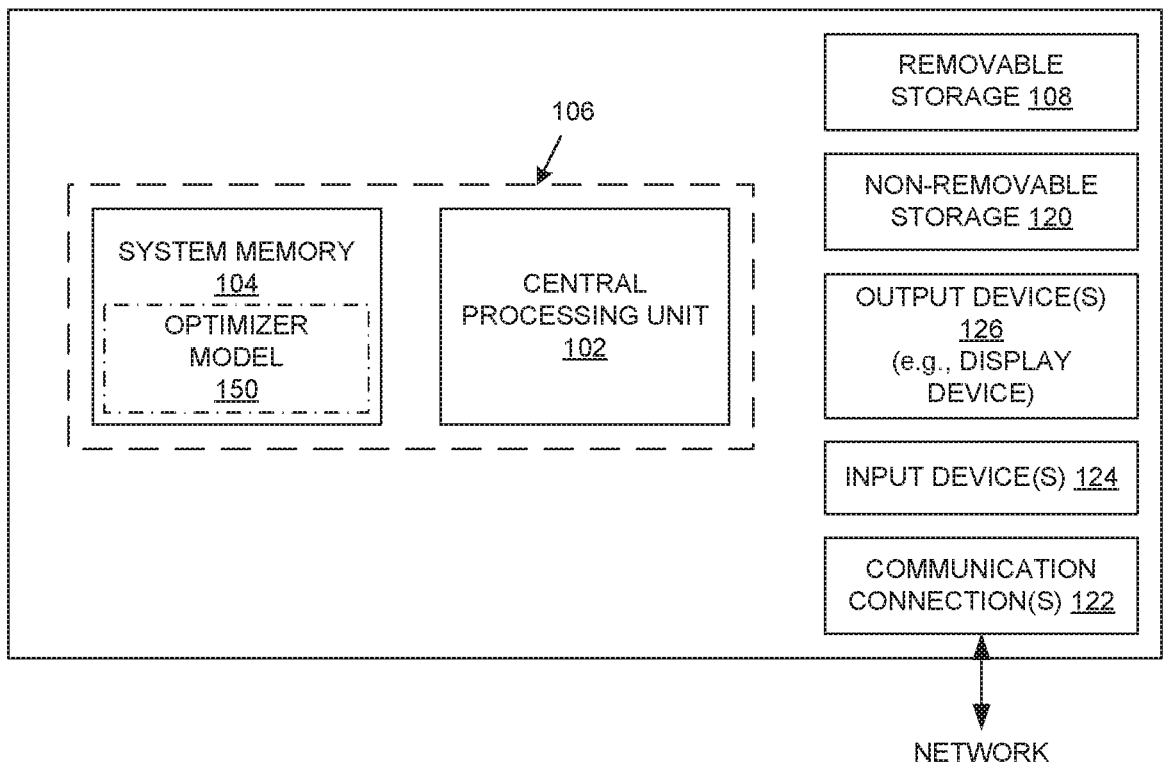
FIG. 1 is a block diagram of an example of a computer system upon which the embodiments described herein may be implemented.

"applying," "indicating," "storing," "using," "adjusting," "including," "computing," "calculating," "determining," "visualizing," "displaying," "rendering," or the like, refer to actions and processes (e.g., the flowcharts of FIGS. 4A, 7, and 8) of a computer system or similar electronic computing device or processor (e.g., the computer system 100 of FIG. 1). The computer system or similar electronic computing device manipulates and transforms data represented as physical (electronic) quantities within the computer system memories, registers or other such information storage, transmission or display devices.

The discussion to follow includes terms such as "dose," "dose rate," "angle," "width," "thickness," "energy," etc. Unless otherwise noted, a value is associated with each such term. For example, a dose has a value and can have different values. For simplicity, the term "dose" may refer to a value of a dose, for example, unless otherwise noted or apparent from the discussion.

Portions of the detailed description that follows are presented and discussed in terms of methods. Although steps and sequencing thereof are disclosed in figures herein (e.g., FIGS. 4A, 7, and 8) describing the operations of those methods, such steps and sequencing are examples only. Embodiments are well suited to performing various other steps or variations of the steps recited in the flowcharts of the figures herein, and in a sequence other than that depicted and described herein.

Embodiments described herein may be discussed in the general context of computer-executable instructions residing on some form of computer-readable storage medium, such as program modules, executed by one or more computers or other devices. By way of example, and not limitation, computer-readable storage media may comprise non-transitory computer storage media and communication media. Generally, program modules include routines, programs, objects, components, data structures, etc., that perform particular tasks or implement particular abstract data types. The functionality of the program modules may be combined or distributed as desired in various embodiments.

Computer storage media includes volatile and nonvolatile, removable and non-removable media implemented in any method or technology for storage of information such as computer-readable instructions, data structures, program modules or other data. Computer storage media includes, but is not limited to, random access memory, read only memory (ROM), electrically erasable programmable ROM (EEPROM), flash memory or other memory technology, compact disk ROM (CD-ROM), digital versatile disks (DVDs) or other optical or magnetic storage devices, or any other medium that can be used to store the desired information and that can accessed to retrieve that information.

Communication media can embody computer-executable instructions, data structures, and program modules, and includes any information delivery media. By way of example, and not limitation, communication media includes wired media such as a wired network or direct-wired connection, and wireless media such as acoustic, radio frequency (RF), infrared and other wireless media. Combinations of any of the above can also be included within the scope of computer-readable media.

FIG. 1 shows a block diagram of an example of a computer system 100 upon which the embodiments described herein may be implemented. In its most basic configuration, the system 100 includes at least one processing unit 102 and memory 104. This most basic configuration is illustrated in FIG. 1 by dashed line 106. The system 100 may also have additional features and/or functionality. For example, the system 100 may also include additional storage (removable and/or non-removable) including, but not limited to, magnetic or optical disks or tape. Such additional storage is illustrated in FIG. 1 by removable storage 108 and non-removable storage 120. The system 100 may also contain communications connection(s) 122 that allow the device to communicate with other devices, e.g., in a networked environment using logical connections to one or more remote computers.

The system 100 also includes input device(s) 124 such as keyboard, mouse, pen, voice input device, touch input device, etc. Some or all of these input devices may be used to control a cursor and to manipulate objects, windows, etc., that are displayed in an output device (e.g., as part of a graphical user interface). Output device(s) 126 such as a display device, speakers, printer, etc., are also included. A display device may be, for example, a cathode ray tube display, a light-emitting diode display, or a liquid crystal display.

In the example of FIG. 1, the memory 104 includes computer-readable instructions, data structures, program modules, and the like associated with an "optimizer" model 150 that is part of a treatment planning system. However, the optimizer model 150 may instead reside in any one of the computer storage media used by the system 100, or may be distributed over some combination of the computer storage media, or may be distributed over some combination of networked computers.

Figure 2:
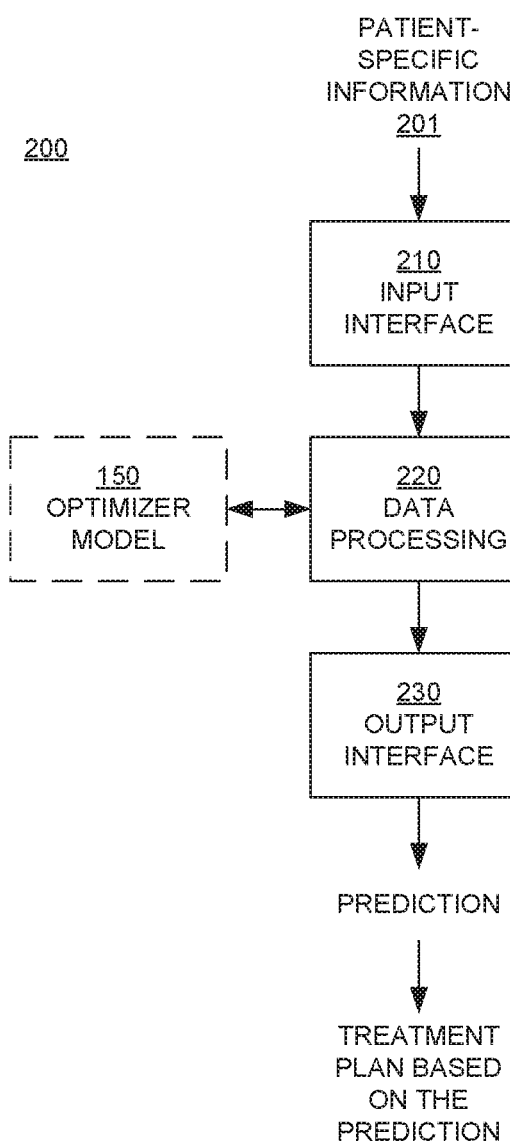
FIG. 2 is a block diagram illustrating an example of an automated radiation therapy treatment planning system in embodiments according to the present invention.

FIG. 2 is a block diagram illustrating an example of an automated radiation therapy treatment planning system 200 in embodiments according to the present invention. The system 200 includes an input interface 210 to receive patient-specific information (data) 201, a data processing component 220 that implements the optimizer model 150, and an output interface 230. The system 200 in whole or in part may be implemented as a software program, hardware logic, or a combination thereof on/using the computer system 100 (FIG. 1).

In the example of FIG. 2, the patient-specific information is provided to and processed by the optimizer model 150. The optimizer model 150 yields a prediction result. A treatment plan based on the prediction result can then be generated.

The discussion to follow refers to, for example, beams energies, angles, ranges, as well as other elements or parameters that have an associated value. The discussion below is in the context of modeled elements and calculated values, unless otherwise noted or made clear in the discussion.

Figure 3:
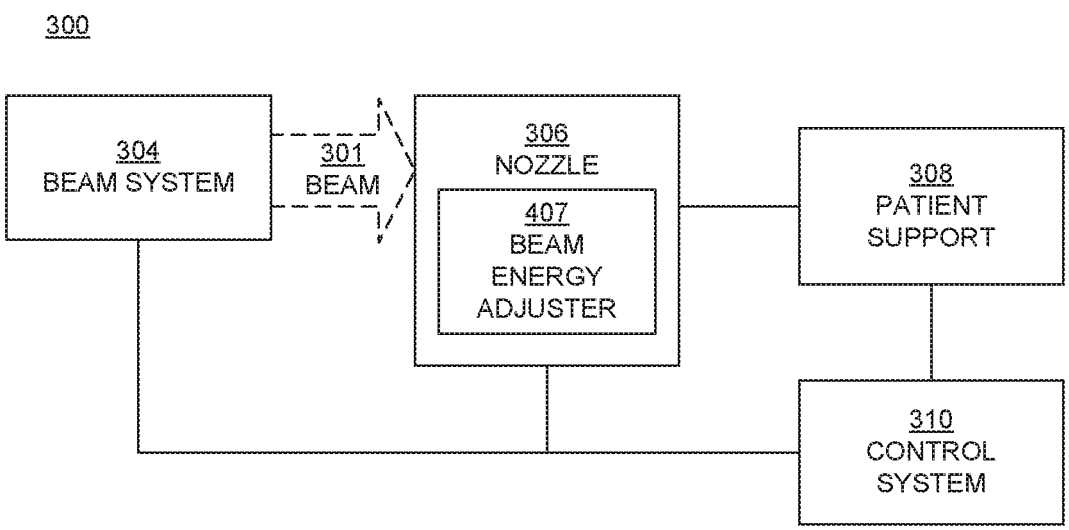
FIG. 3 is a block diagram showing selected components of a radiation therapy system upon which embodiments according to the present invention can be implemented.

FIG. 3 is a block diagram showing selected components of a radiation therapy system 300 that can be used to implement radiation treatment plans developed in embodiments according to the present invention. In the example of FIG. 3, the system 300 includes a beam system 304 and a nozzle 306.

The beam system 304 generates and transports a beam 301. The beam 301 can be a proton beam, electron beam, photon beam, ion beam, or atom nuclei beam (e.g., carbon, helium, and lithium). In embodiments, depending on the type of beam, the beam system 304 includes components that direct (e.g., bend, steer, or guide) the beam system in a direction toward and into a nozzle 306. In embodiments, the radiation therapy system may include one or more multileaf collimators (MLCs); each MLC leaf can be independently moved back-and-forth by the control system 310 to dynamically shape an aperture through which the beam can pass, to block or not block portions of the beam and thereby control beam shape and exposure time. The beam system 304 may also include components that are used to adjust (e.g., reduce) the beam energy entering the nozzle 306.

The nozzle 306 is used to aim the beam toward various locations (e.g., a volume in a treatment target in a patient) supported on the patient support device 308 (e.g., a chair or table) in a treatment room. The nozzle 306 may be mounted on or a part of a gantry (not shown) that can be moved relative to the patient support device 308, which may also be moveable.

A volume in a treatment target may include the entire treatment target, and may be an organ, a portion of an organ (e.g., a volume or region within the organ), a tumor, diseased tissue, or a patient outline. A volume in a treatment target may include both unhealthy tissue (e.g., a tumor) and healthy tissue. A volume in a treatment target may be divided (virtually) into a number of voxels. A sub-volume can include a single voxel or multiple voxels.

The control system 310 of FIG. 3 receives and implements a prescribed radiation treatment plan. In embodiments, the control system 310 includes a computer system having a processor, memory, an input device (e.g., a keyboard), and perhaps a display in well-known fashion. The control system 310 can receive data regarding operation of the system 300. The control system 310 can control parameters of the beam system 304, nozzle 306, and patient support device 308, including parameters such as the energy, intensity, direction, size, and/or shape of the beam, according to data it receives and according to the prescribed radiation treatment plan.

As noted above, the beam 301 entering the nozzle 306 has a specified energy. Thus, in embodiments according to the present disclosure, the nozzle 306 includes one or more components that affect (e.g., decrease, modulate) the energy of the beam. The term "beam energy adjuster" is used herein as a general term for a component or components that affect the energy of the beam, in order to control the range of the beam (e.g., the extent that the beam penetrates into a target), to control the dose delivered by the beam, and/or to control the depth versus depth curve of the beam, depending on the type of beam. For example, for a proton beam or an ion beam that has a Bragg peak, the beam energy adjuster can control the location and shape of the Bragg peak in the volume in a treatment target. In various embodiments, the beam energy adjuster 307 includes a range modulator, a range shifter, or both a range modulator and a range shifter. In other embodiments, energy modulation is performed outside of the nozzle (e.g. upstream of the nozzle).

In radiation therapy techniques in which the intensity of the particle beam is either constant or modulated across the field of delivery, such as in intensity modulated radiation therapy (IMRT) and intensity modulated particle therapy (IMPT), beam intensity is varied across each treatment region (volume in a treatment target) in a patient. Depending on the treatment modality, the degrees of freedom available for intensity modulation include, but are not limited to, beam shaping (e.g., width and range) and angle of incidence (which may be referred to as beam geometry). These degrees of freedom lead to an effectively infinite number of potential treatment plans, and therefore consistently and efficiently generating and evaluating high-quality treatment plans is beyond the capability of a human and relies on the use of a computer system, particularly considering the time constraints associated with the use of radiation therapy to treat ailments like cancer, as well as the large number of patients that are undergoing or need to undergo radiation therapy during any given time period.

The beam 301 can have virtually any regular or irregular cross-sectional (e.g., beam's eye view) shape. For example, the cross-sectional shape of the beam 301 can be defined using an MLC that blocks a portion or portions of the beam. Different beams can have different cross-sectional shapes. Also, for a proton beam or an ion beam that has a Bragg peak, the shape of the Bragg peak (e.g., the width or depth of the Bragg peak in the direction of the beam, and the amplitude or amount of dose as a function of that depth) in the volume in a treatment target can be defined using the beam energy adjuster, and different beams can have different Bragg peak shapes.

In embodiments, the beam 301 includes a number of beam segments or beam lets (that also may be referred to as spots). A maximum energy (e.g., 80 MeV) is specified for the beam 301, and an energy level is defined for each of the beam segments as a percentage or fraction of the maximum energy. In essence, each of the beam segments is weighted in terms of its energy level; some beam segments are weighted to have a higher energy level than other beam segments. By weighting the energy per beam segment, in effect the intensity of each beam segment is also weighted. The defined energy level or intensity can be realized for each beam segment using the beam energy adjuster 307.

Each beam segment can deliver a relatively high dose rate (a relatively high dose in a relatively short period of time). For example, each beam segment can deliver at least 40 grays (Gy) in less than one second, and may deliver as much as 120 Gy per second or more.

A single beam may be used and applied from different directions and in the same plane or in different planes. Alternatively, multiple beams may be used, in the same plane or in different planes. The directions and/or numbers of beam can be varied over a number of treatment sessions (that is, fractionated in time) so that a uniform dose is delivered across the volume in the treatment target. The number of beams delivered at any one time depends on the number of gantries or nozzles in the radiation treatment system (e.g., the radiation treatment system 300 of FIG. 3) and on the treatment plan.

Methods and Systems Used for Planning Radiation Treatment

Embodiments according to the present invention provide improved methods that can be used for generating and evaluating radiation treatment plans for radiation therapy including FLASH RT. For FLASH RT, dose rates of at least 40 Gy in less than one second, and as much as 120 Gy per second or more, may be used.

A proposed radiation treatment plan is defined (e.g., using the optimizer model 150 of FIGS. 1 and 2), stored in a computer system memory, and accessed from that memory. The proposed radiation treatment plan includes values of parameters that can affect dose and dose rate, as well as other parameters. The parameters that can affect dose and dose rate include, but are not limited to, a number of irradiations of the volume in a treatment target, a duration of each of the irradiations (irradiation times), and a dose deposited in each of the irradiations. The parameters may also include angles (directions) of beams to be directed toward a treatment target, and a beam energy for each of the beams. The parameters may also include a period of time during which the irradiations are applied (e.g., a number of irradiations are applied over a period of time such as an hour, with each irradiation in the period of time separated from the next by another period of time) and an interval of time between each period of irradiations (e.g., each hour-long period is separated from the next by a day). The volume of a treatment target is divided into sub-volumes or voxels, in which case the values of the parameters can be on a per-sub-volume or per-voxel basis (e.g., a value per sub-volume or voxel).

Computer-implemented methods for planning radiation treatment in embodiments according to the invention are used to identify, for a given isocenter and given beam energy, beam delivery angles where beam fields satisfy a criterion for transmission fields (beam fields with a Bragg peak significantly or entirely outside of a patient's body). Those beam angles can be determined and evaluated before dose calculations are performed. Consequently, treatment planning can be performed more efficiently by eliminating or avoiding beam angles that have a radiological thickness that is too large to satisfy the transmission field criterion (that is, that would place the Bragg peak inside the body). Radiological thickness may be expressed as a water-equivalent distance or thickness or ratio.

Figure 4A:
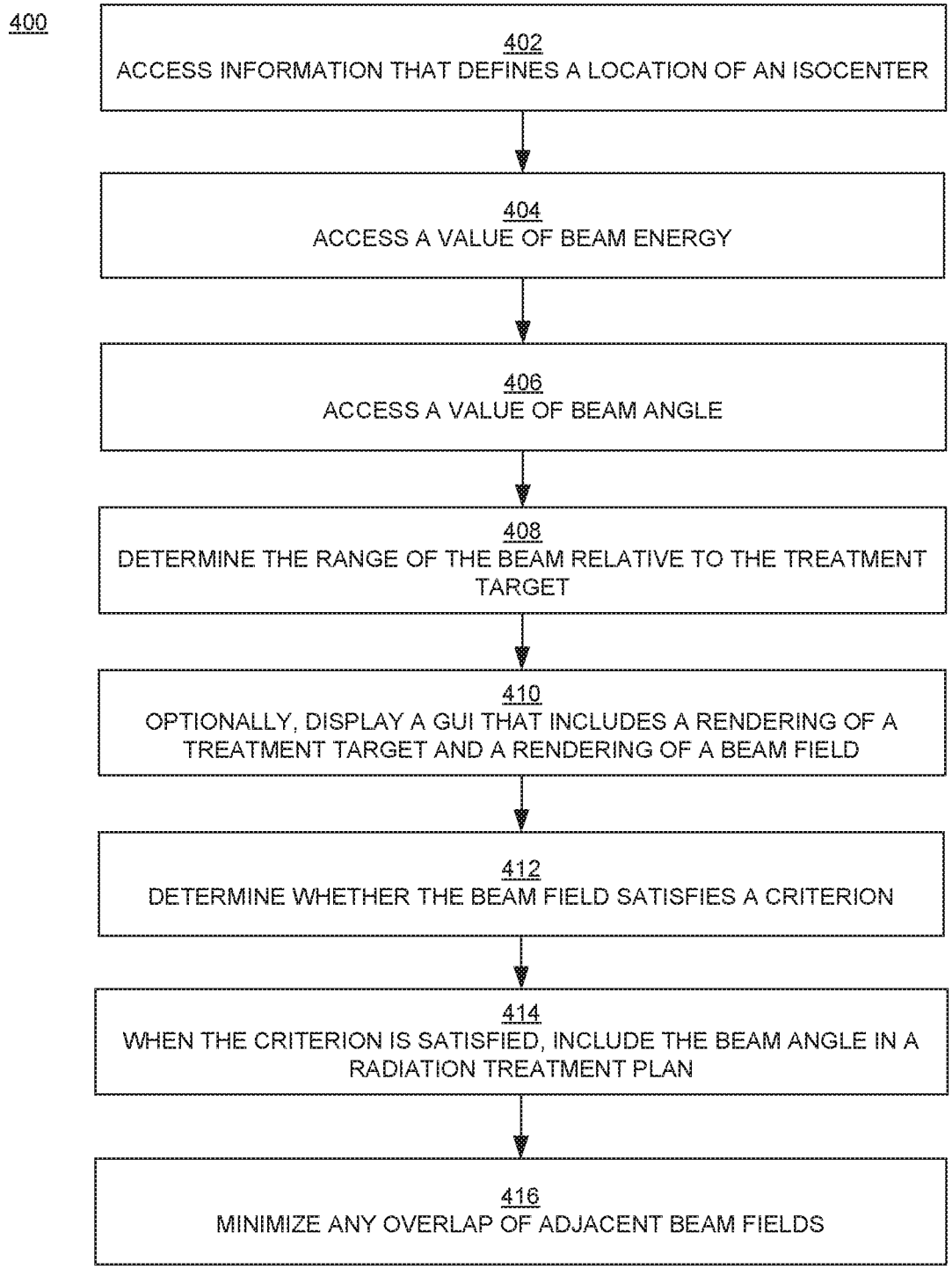
FIG. 4A is a flowchart of an example of computer-implemented operations for radiation treatment planning in embodiments according to the present invention.

FIG. 4A is a flowchart 400 of an example of a computer-implemented method that can be used for radiation treatment planning in embodiments according to the present invention. The flowchart 400 can be implemented as computer-executable instructions (e.g., the optimizer model 150 of FIG. 1) residing on some form of computer-readable storage medium (e.g., in memory of the computer system 100 of FIG. 1).

In block 402 of FIG. 4A, information that defines a location of an isocenter that is based on the location of a treatment target is accessed (e.g., from computer system memory).

In block 404, a value of beam energy for a beam of radiation is accessed (e.g., from computer system memory).

In block 406, a value of an angle of the beam relative to the treatment target is accessed (e.g., from computer system memory).

In block 408, in embodiments, the range of the beam, including the location of the Bragg peak, is determined relative to the treatment target using a radiological thickness (e.g., water-equivalent distance or water-equivalent thickness) for the location of the treatment target. In other embodiments, the location of the Bragg peak relative to the treatment target can be calculated based on a dose calculation (e.g., by the optimizer model 150 of FIG. 1). The radiological thickness is determined based on the specified beam energy (block 404).

Figure 5:
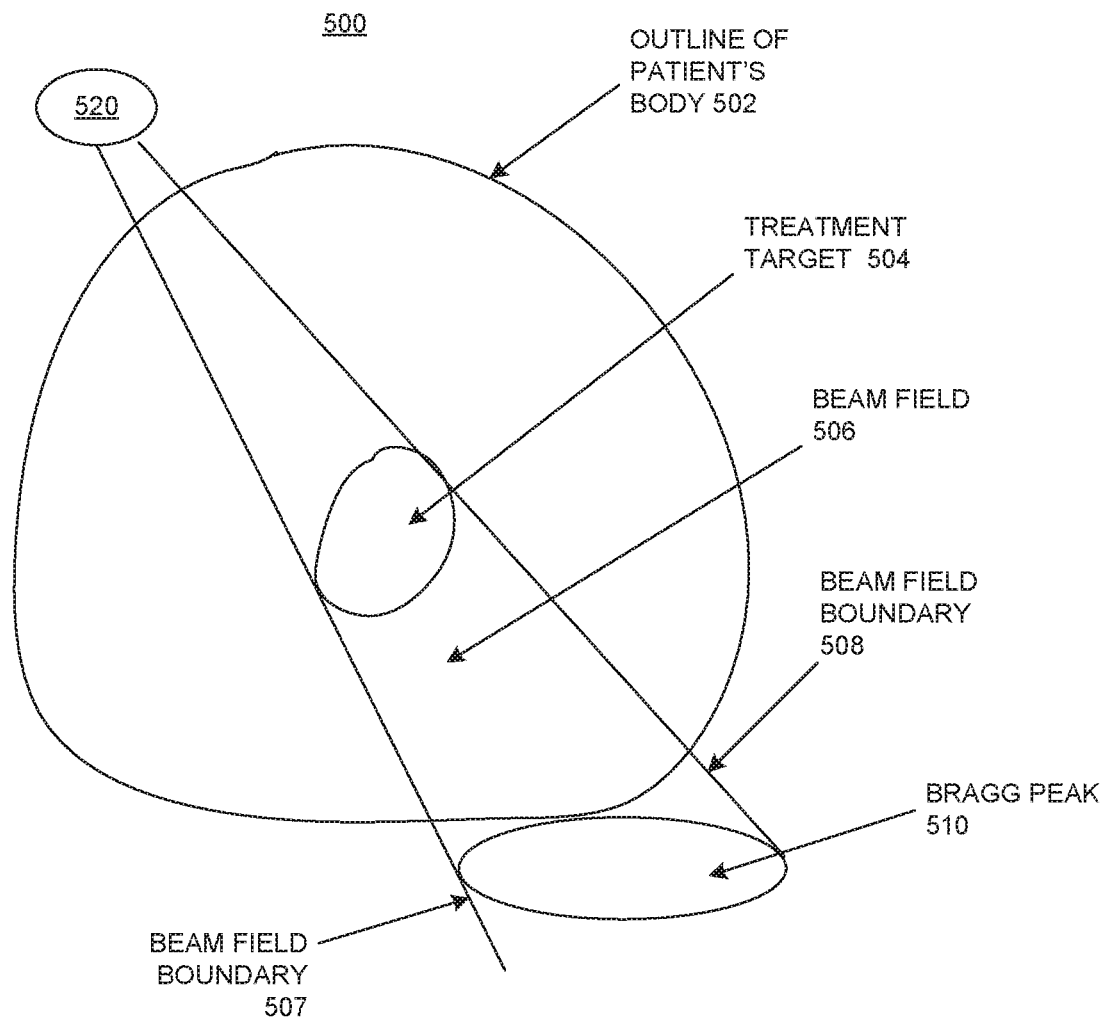
FIGS. 5 and 6 are examples of graphical user interfaces on a display device and used for planning radiation treatment in embodiments according to the present invention.
Figure 6:
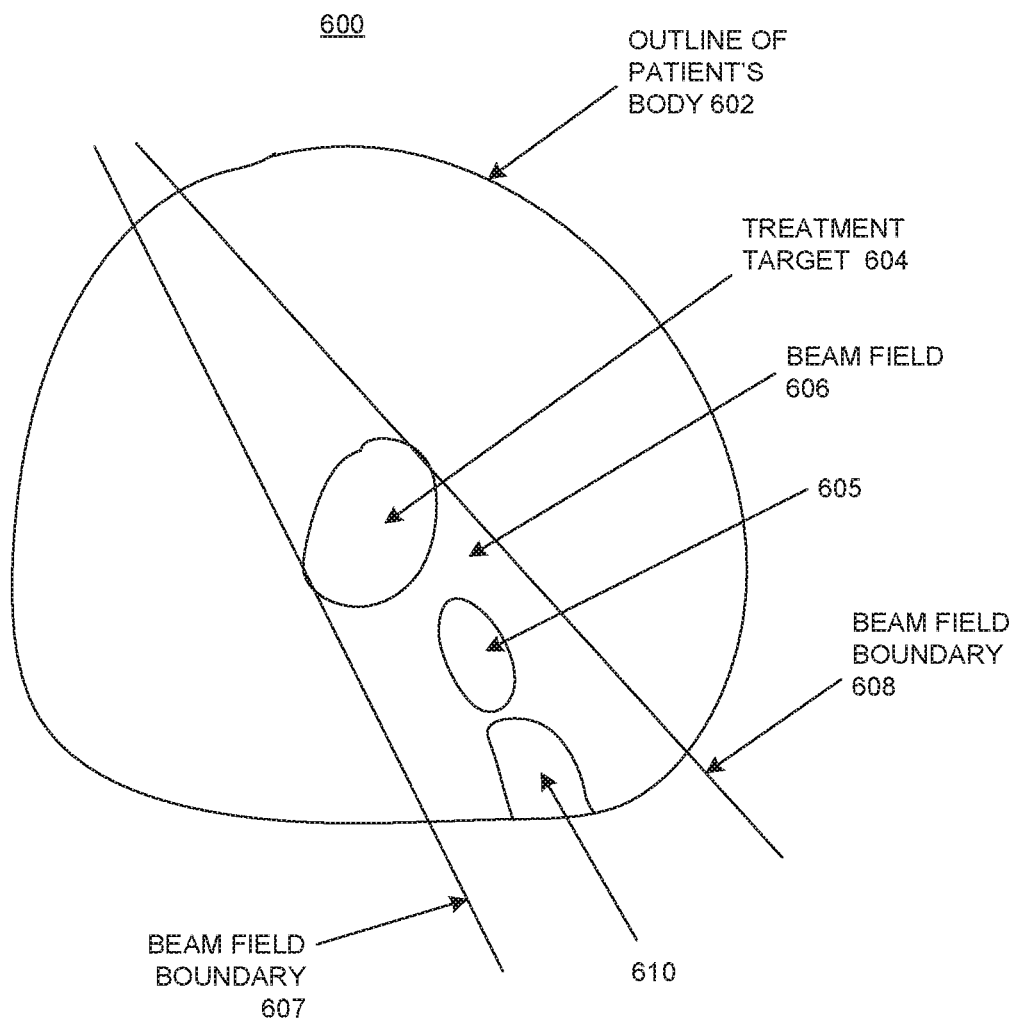

In block 410, in embodiments, a graphical user interface (GUI) that includes a rendering of the treatment target, and also includes a rendering of a field of the beam relative to the treatment target, is displayed (e.g., on a computer system display device). Examples of GUIs in embodiments according to the invention are shown in FIGS. 5 and 6 and are discussed further below. In embodiments, the beam includes a number of beam lets, in which case the rendered field of the beam can include the field of each beam let, or the rendered field of the beam can be a composite representation of the beam lets. Alternatively, the rendered beam field can be based on the center of the beam.

In embodiments in which the GUI is displayed, the rendering of the field of the beam in the GUI indicates a location in the field of the Bragg peak. In embodiments, the rendering of the field of the beam in the GUI shows the range and coverage of the field relative to the treatment target. In such embodiments, the rendering of the field of the beam in the GUI also shows the width (lateral size) of the field. Additional information is provided in the discussion of FIG. 7.

Each beam field rendered in the GUI can be moved to different positions (different angles) in the GUI using, for example, a cursor and cursor-control device, and the rendered range of the beam field is changed accordingly, to account for changes in the type of tissue that the beam field encounters when the angle is changed. The GUI thus allows a user to readily determine the location of the Bragg peak for each beam field, to thereby determine which beam fields (and which beam angles) satisfy the transmission field criterion.

The width of the beam field rendered in the GUI can be adjusted. For example, if only part of a beam field is acceptable in terms of satisfying the transmission field criterion, then the width of the beam field can be narrowed by user interaction with the GUI, so that the width of the beam instead corresponds to the acceptable part. For example, a user can move the boundaries or edges of the beam field using a cursor guided by a cursor control device (e.g., a mouse).

In block 412 of FIG. 4A, a determination is made with regard to whether or not the field of the beam satisfies a criterion. In embodiments, the criterion (which may be referred to herein as the transmission field criterion) corresponds to an amount of the beam field's Bragg peak that is outside a patient's body, and the criterion is satisfied when a threshold amount of the Bragg peak is outside the patient (e.g., all of, or X percent of, the Bragg peak is outside the body).

The determination of block 412 can be made using the results of the operations from block 408 and/or using the GUI of block 410. For example, in either case, a measure of the area of the Bragg peak that is outside of the patient's body, as a fraction or percentage of the total area of the Bragg peak, can be determined using the optimizer model 150 (FIGS. 1 and 2), and the value of that measure can be stored in computer system memory and/or displayed in the GUI. The value of that measure can be compared to the threshold amount by the optimizer model 150, and if that value satisfies (e.g., is less than) the threshold amount, then the transmission field criterion is satisfied. The comparison of the value of the measure can be performed by the optimizer model 150 and/or based on the visual representation in the GUI.

Figure 4B:
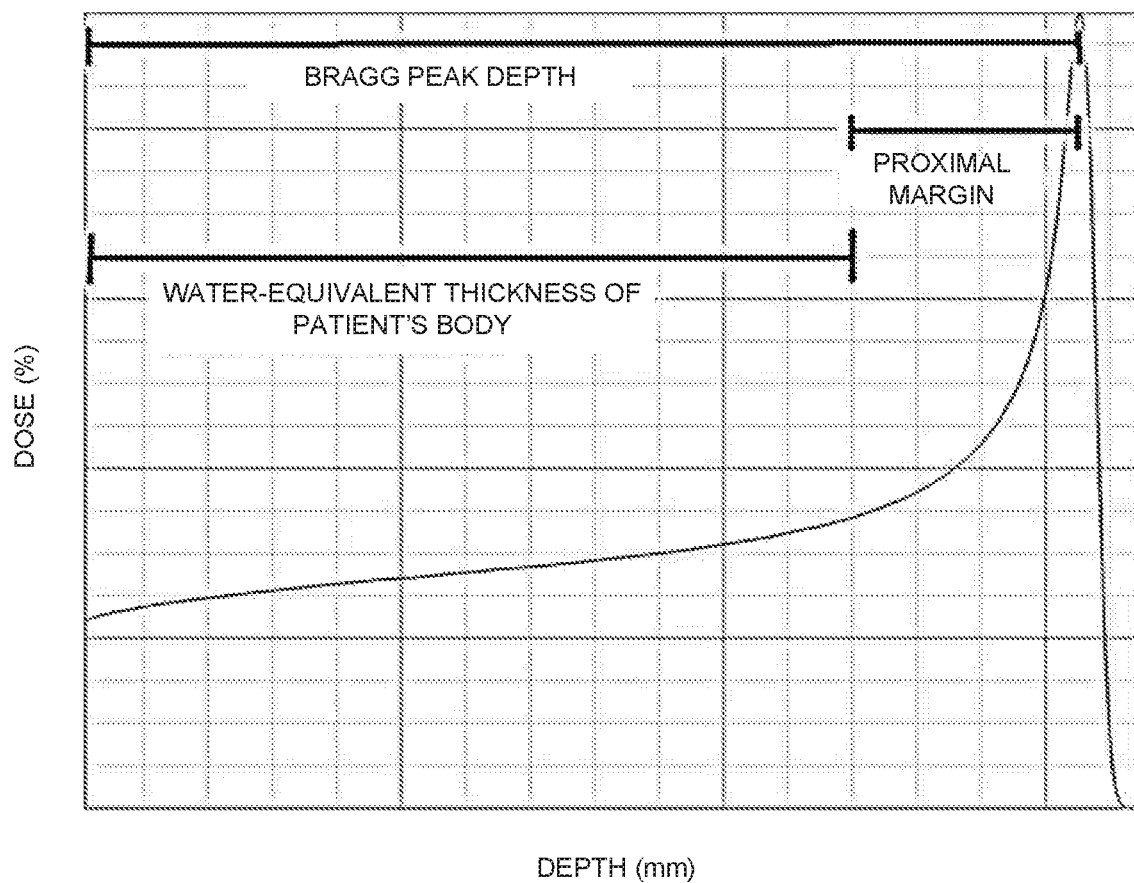
FIG. 4B illustrates an example of dose versus depth in embodiments according to the invention.

FIG. 4B illustrates an example of dose (e.g., as a percentage versus depth (e.g., in millimeters, mm) in embodiments according to the invention. FIG. 4B shows the water-equivalent thickness of the patient's body, specifically the maximum water-equivalent thickness). FIG. 4B also shows the location (depth) of the Bragg peak. The difference between the Bragg peak depth and the water-equivalent thickness of the patient's body is referred to herein as the proximal margin. In embodiments, the proximal margin establishes the threshold amount discussed above. That is, when the difference between the Bragg peak depth and the water-equivalent thickness of the patient's body is at least equal to the proximal margin, then the transmission field criterion is satisfied. In an embodiment, the proximal margin is a user-defined setting.

As an alternative to or in addition to using a proximal margin, a distal margin is used. The distal margin establishes a distance between the distal surface of the patient's body (relative to the beam source) and the Bragg peak. Thus, for example, a large value for the distal margin would indicate that the Bragg peak is far outside the patient's body. In an embodiment, the distal margin is calculated based on user-defined settings. The distal margin can be used during radiation treatment planning to determine the robustness of the transmission plan. The distal margin can be estimated by calculating the Bragg peak location in a virtual bolus at the beam exit. The material of the virtual bolus may be user-definable. In general, a user may want to use material similar to the tissue in the beam exit region. The user may set a value above which the distal margin needs to be for a beam that qualifies as a transmission field.

In block 414 of FIG. 4A, when the criterion is satisfied, the value of the angle of the beam is included in a proposed or final radiation treatment plan. Additional information is provided in the discussion of FIG. 8.

In block 416 of FIG. 4A, any overlap of adjacent beam fields is minimized.

FIGS. 5 and 6 illustrate examples of GUIs 500 and 600, respectively, that can be used to display information associated with planning radiation treatment in embodiments according to the present invention. The GUIs can be generated using the methods described herein, implemented using computer-executable instructions (e.g., the optimizer model 150 of FIG. 1) residing on some form of computer-readable storage medium (e.g., memory of the computer system 100 of FIG. 1), and displayed on the output device 126 of the computer system.

Embodiments according to the present invention are not limited to the GUIs illustrated in FIGS. 5 and 6. In general, GUIs in embodiments according to the present invention allow beam fields and the locations of their associated Bragg peaks to be visualized relative to a treatment target.

Also, the disclosed GUIs can include information in addition to that included in the examples.

In embodiments, drop-down menus or other types of GUI elements (not shown in the figures) can be used to select and establish settings (e.g., attributes, thresholds, etc.) for the GUIs and the type(s) of information to be displayed at any one time.

Also, the GUIs are not necessarily static displays. For example, the information presented in the GUIs can be programmed to change in response to user inputs. Also, for example, the GUIs can be programmed to present different cross-sectional slices of the volume in a treatment target in sequence to provide a depth dimension to a two-dimensional representation, or to manipulate (e.g., rotate) a virtual three-dimensional representation so that it can be viewed from different perspectives.

In the example of FIG. 5, the GUI 500 includes renderings of the outline 502 of a cross-section of the patient's body (e.g., viewed from the head down) and an outline 504 of the treatment target. Although they do not appear in the example of FIG. 5, other structures or volumes in the patient's body may also be rendered in the GUI 500.

The GUI 500 also includes renderings of a beam field 506 and a location 510 of the Bragg peak in that beam field. In this example, the boundaries of the beam field 506 are delineated by the lines 507 and 508. The range or depth of the beam field 506 is determined by the radiation thickness (e.g., water-equivalent distance) of the tissue traversed by the beam field. Thus, the GUI 500 allows the range, coverage, and width of the beam field 506 to be readily visualized relative to the patient's body and the treatment target.

In the example of FIG. 5, the Bragg peak is entirely outside the patient's body, and so the beam field 506 satisfies the transmission field criterion and is therefore a potential candidate for further evaluation as part of the radiation treatment planning process. As mentioned above, the Bragg peak does not necessarily have to be entirely outside the patient's body in order for the beam field to be a potential candidate for further evaluation, depending on how the transmission field criterion is defined.

In embodiments, a user can dynamically change the angle of the beam field 506 relative to the patient's body and treatment target. For example, the angle of the beam field 506 relative to the treatment target 504 can be changed by changing the positions of the ends of the lines 507 and 508 and/or by "dragging" the GUI element 520 to a different position using a cursor and cursor-control device, for example. Similarly, the width of the beam field can be changed by dragging either or both of the lines 507 and 508 to a different position.

When the position or dimensions of the beam field 506 are changed, the range of the beam field and the location of the Bragg peak are automatically recalculated to account for any change in the radiological thickness, and the GUI 500 is updated accordingly. Similarly, if the specified isocenter and/or beam energy is changed to a different value, then the range of the beam field and the location of the Bragg peak are automatically recalculated, and the GUI 500 is updated accordingly. In general, when a user changes information that has an effect on the information displayed in the GUI 500, then the displayed information is changed. Thus, users are provided real-time visual feedback on the effect of such changes, and can quickly determine when criteria such as the transmission field criterion are or are not being satisfied.

In the example of FIG. 6, the GUI 600 includes renderings of the outline 602 of a cross-section of the patient's body (e.g., viewed from the head down) and an outline 604 of the treatment target. The GUI 600 also includes a rendering of an outline 605 of a structure or organ that has an effect on the radiological thickness of the beam field 606; that is, the structure or organ attenuates the incident beam. In this example, the range of the beam field 606 is reduced in the region behind that structure or organ. Thus, the beam field 606 does not reach (cover) the region within the outline 610. This would imply that the Bragg peak of the beam, at least in the region affected by the structure or organ, is within the patient's body and does not satisfy the transmission field criterion. A user can change the boundaries of the beam field 606 by moving either or both of the lines 607 and 608, to determine whether at least part of the beam field satisfies criteria such as the transmission field criterion.

Figure 7:
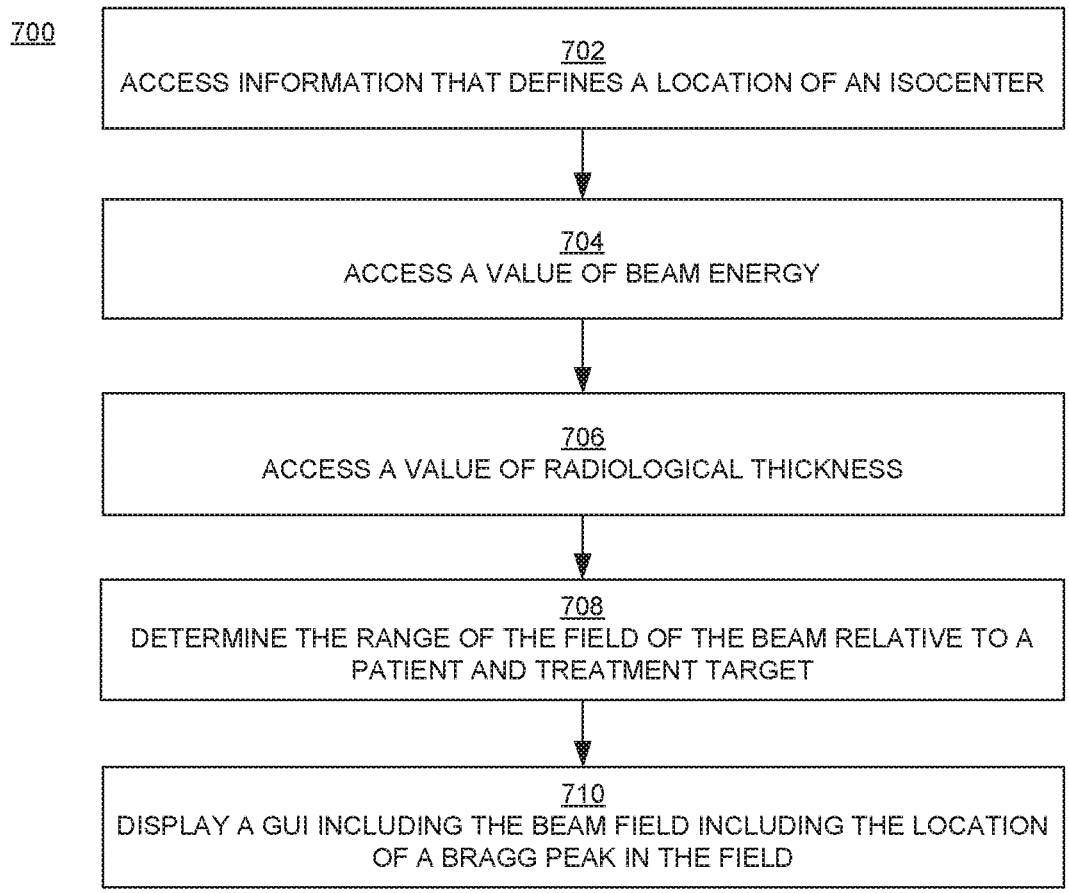
FIGS. 7 and 8 are flowcharts of examples of computer-implemented operations for radiation treatment planning in embodiments according to the present invention.
Figure 8:
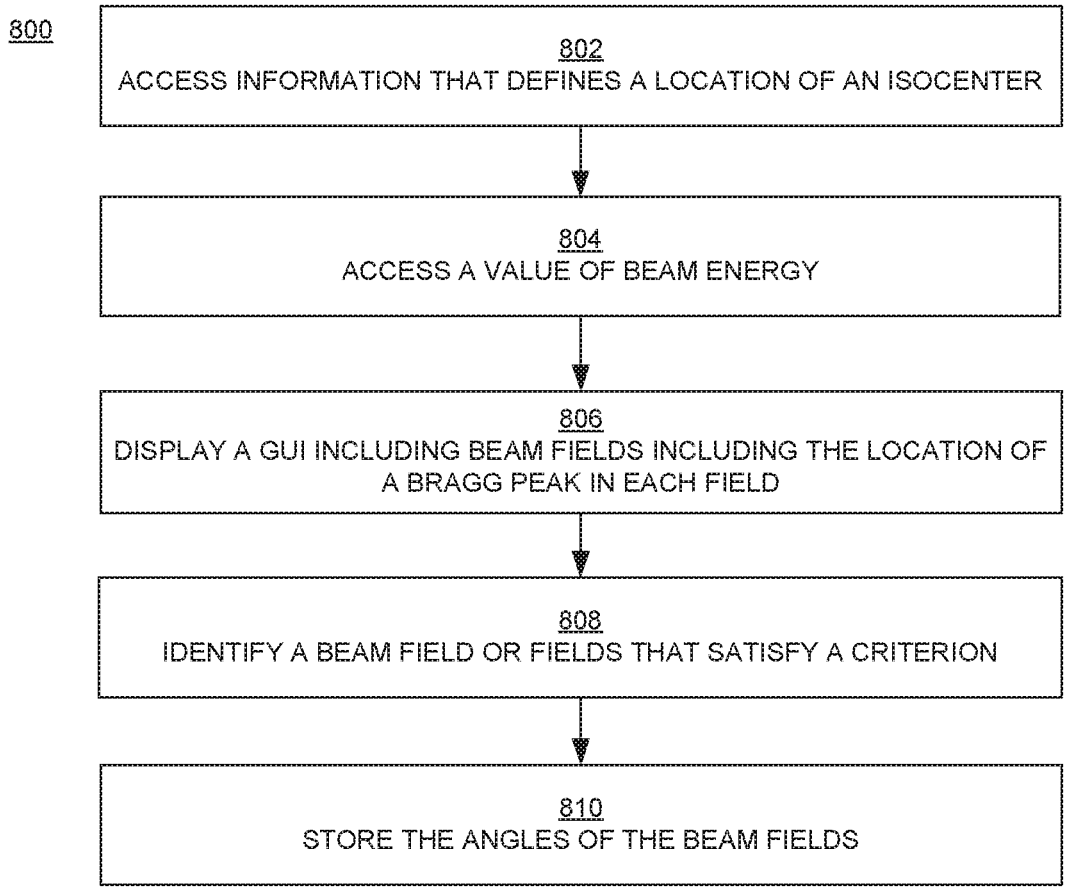
Figure 9A:
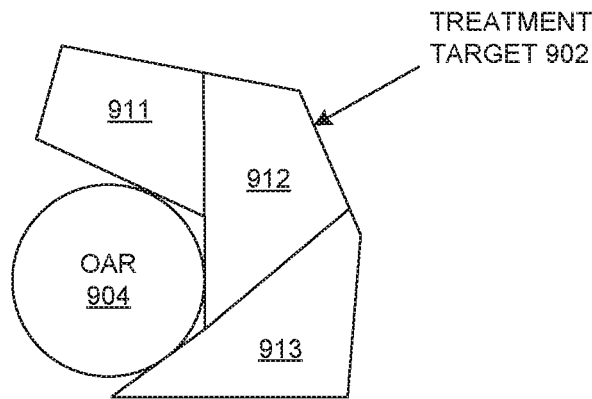
FIGS. 9A, 9B, 9C, and 9D illustrate an example of patch fielding in embodiments according to the invention.
Figure 9B:
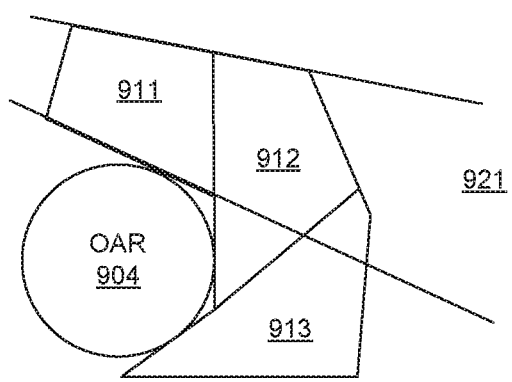
Figure 9C:
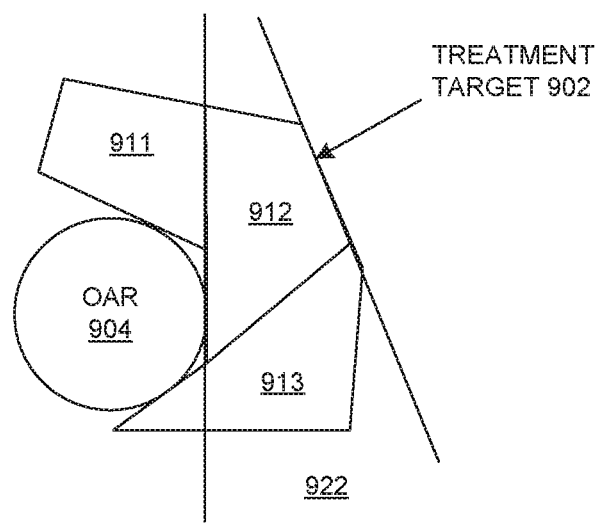
Figure 9D:
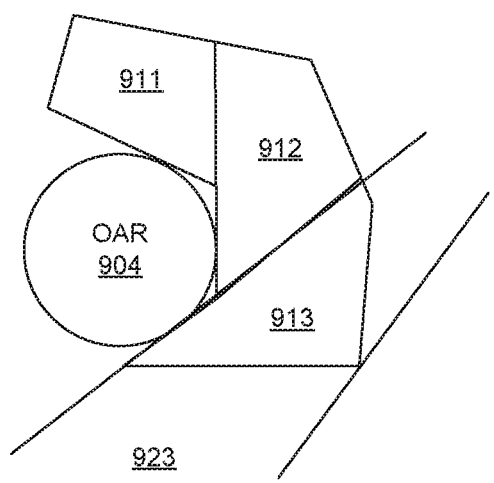

FIGS. 7 and 8 are flowcharts 700 and 800, respectively, of examples of computer-implemented methods used for planning radiation treatment in embodiments according to the present invention. The flowcharts 700 and 800 can be implemented as computer-executable instructions (e.g., the optimizer model 150 of FIG. 1) residing on some form of computer-readable storage medium (e.g., in memory of the computer system 100 of FIG. 1).

In block 702 of FIG. 7, information that includes a location of an isocenter that is based on a location of a treatment target is accessed (e.g., from computer system memory).

In block 704, information that includes a value of beam energy for a beam of radiation is accessed (e.g., from computer system memory).

In block 706, information that includes a value of radiological thickness associated with the path of the beam is accessed (e.g., from computer system memory) or calculated.

In block 708, using the value of radiological thickness and the value of beam energy, the range of a field of the beam along the path and relative to the treatment target and the patient is determined. Significantly, because the range of the beam field is determined using a respective value of radiological thickness for the field, it is not necessary to perform dose calculations at this stage of the radiation treatment planning process. The location of the Bragg peak in the beam field can also be determined.

In block 710, in some embodiments, a GUI (e.g., see FIGS. 5 and 6) that includes a rendering of the treatment target and also includes a rendering of the beam field is displayed (e.g., on a computer system display device). In embodiments, the rendering of the beam field indicates the location of the Bragg peak in the field.

In block 802 of FIG. 8, information that includes a location of an isocenter that is based on a location of a treatment target is accessed (e.g., from computer system memory).

In block 804, information that includes a value of beam energy for a beam of radiation is accessed (e.g., from computer system memory).

In block 806, in some embodiments, a GUI (e.g., see FIGS. 5 and 6) that includes a rendering of the treatment target and also includes a rendering of fields of the beam is displayed (e.g., on a computer system display device), where the fields are at different angles relative to the treatment target. In embodiments, the rendering of the beam fields indicates a location of a respective Bragg peak in each of the fields. In embodiments, the rendering of the beam fields shows a range of each field and coverage of each field relative to the treatment target. Significantly, the range of each field is determined using a respective value of radiological thickness for the field. As such, it is not necessary to perform dose calculations at this stage of the radiation treatment planning process.

In block 808 of FIG. 8, a subset (one or more) of the beam fields that satisfy a criterion (e.g., the transmission field criterion described above) is identified.

In block 810, values of the angles of the fields in the subset are stored (e.g., from computer system memory). The angles of the fields in the subset can be used in other stages of the radiation treatment planning process. Thus, embodiments according to the invention limit the solution space around the isocenter; that is, the number of beam fields that need to be considered in subsequent stages of the radiation treatment planning process is reduced. The solution space can be further reduced by considering only angles that minimize the overlap between adjacent beam fields.

A transmission check provides input for optimizing beam angles. The transmission check can be part of the evaluation of the robustness of a proposed treatment plan. The transmission check can be combined with a collision check.

For a given isocenter and position of the patient support device, embodiments according to the invention determine, in three dimensions, all gantry angles for which the beam let at the central axis of the beam passes the transmission check and, in some embodiments, visualize such results in a GUI. Alternatively, a user can define an area around the central axis that is used instead of the beamlet at the central axis.

In embodiments, the dose optimizer module 150 (FIG. 1) provides spatial information about the location of the Bragg peak. The dose optimizer model 150 can provide a dose distribution that contains only the dose that was deposited at the Bragg peak of a given beam let. In addition to the transmission check, this information may be valuable for non-transmission fields, as the biological effect at the Bragg peak is expected to be different than that in the transmission region.

While the operations in the flowcharts of FIGS. 4A, 7, and 8 are presented as occurring in series and in a certain order, the present invention is not so limited. The operations may be performed in a different order and/or in parallel, and they may also be performed in an iterative manner. As noted above, because of the different parameters that need to be considered, the range of values for those parameters, the interrelationship of those parameters, the need for treatment plans to be effective yet minimize risk to the patient, and the need to generate high-quality treatment plans quickly, the use of the optimizer model 150 executing consistently on the computer system 100 (FIG. 1) for radiation treatment planning as disclosed herein is important.

FIGS. 9A, 9B, 9C, and 9D illustrate an example in which the methods described above are used to determine beam fields in patch fielding in embodiments according to the invention. The information in FIGS. 9A-9D can be displayed as a GUI analogous to those described above (FIGS. 5 and 6), and the information rendered in such a GUI can be dynamically changed as described above.

Continuing with reference to FIGS. 9A-9D, patch fielding is useful when the treatment target 902 partially surrounds or encircles an organ-at-risk (OAR) 904. In the example of FIGS. 9A-9D, the treatment target 902 is divided into sub-volumes 911, 912, and 913, and those sub-volumes are irradiated from different directions (angles) by beam fields 921, 922, and 923, respectively, that do not cover the OAR 904, thus sparing the OAR. The methods and GUIs described above (FIGS. 4A, 4B, and 5-8) can be applied to each of the beam fields 921, 922, and 923, and thereby allow a user to readily determine and/or visualize in real time whether each of those beam fields satisfy criteria such as the transmission field criterion while sparing the OAR 904.

In summary, embodiments according to the invention improve radiation treatment planning and the treatment itself. Treatment plans generated as described herein are superior for sparing normal tissue from radiation in comparison to conventional techniques even for non-FLASH dose rates by reducing, if not minimizing, the magnitude (and the integral in some cases) of the dose to normal tissue (outside the target) by design. When used with FLASH dose rates, management of patient motion is simplified because the doses are applied in a short period of time (e.g., less than a second). Treatment planning, while still a complex task of finding a balance between competing and related parameters, is simplified relative to conventional planning. The techniques described herein may be useful for stereotactic radiosurgery as well as stereotactic body radiotherapy with single or multiple metastases.

In addition to those benefits, in some embodiments, a GUI facilitates treatment planning by allowing a planner to readily visualize key elements of a proposed treatment plan (e.g., the dose rate per sub-volume), to readily visualize the effects on those elements of changes to the proposed plan, and to readily visualize a comparison between different plans.

Embodiments according to the invention are not necessarily limited to radiation therapy techniques such as IMRT and IMPT.

Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims.

What is claimed is:

1. A computer system, comprising:
  a processor;
  a display device coupled to the processor; and
  a memory coupled to the processor, the memory storing
    instructions that, when executed, cause the processor to perform a method used for planning radiation treatment, the method comprising:

accessing information comprising a location of an isocenter based on a location of a treatment target;

accessing information comprising a value of beam energy for a beam of radiation and also comprising a value of an angle of the beam relative to the treatment target;

determining a range of a field of the beam relative to the treatment target using the isocenter and the angle;

determining whether the range of the field of the beam satisfies a criterion, the criterion being an amount of a Bragg peak outside of a patient's body;

including the value of the angle of the beam in a plan for radiation treatment in response to the criterion being satisfied; and displaying, on the display device, a graphical user interface (GUI) including a rendering of the treatment target and a rendering of the range of the field of the beam relative to the treatment target, the rendering of the range of the field of the beam being adjustable with respect to the rendering of the treatment target to determine whether the range of the field of the beam satisfies the criterion.

2. The computer system of claim 1, wherein the rendering of the range of the field of the beam indicates a location in the field of a Bragg peak of the beam.

3. The computer system of claim 1, wherein the rendering of the field of the beam shows coverage of the field relative to the treatment target.

4. The computer system of claim 3, wherein the method further comprises accessing information including a value for a width of the beam, wherein the rendering of the field of the beam shows the width of the beam.

5. The computer system of claim 1, wherein the range is determined using a value of radiological thickness for the location of the treatment target.

6. The computer system of claim 1, wherein the criterion is satisfied when a threshold amount of the Bragg peak is outside the patient's body.

7. The computer system of claim 1, wherein the method further comprises minimizing overlap of the field of the beam and an adjacent field of a beam.

8. The computer system of claim 1, wherein the beam comprises a plurality of beamlets, wherein the field of the beam comprises a field of each beamlet of the plurality of beamlets.

9. A non-transitory computer-readable storage medium having computer-executable instructions for causing a computer system to perform a method used for planning radiation treatment, the method comprising:

accessing information comprising a location of an isocenter that is based on a location of a treatment target;

accessing information comprising a value of beam energy for a beam of radiation;

displaying, on a display device of the computer system, a graphical user interface (GUI) comprising a rendering of the treatment target and also comprising a rendering of a plurality of fields of the beam, wherein the fields are at different angles relative to the treatment target, the rendering of the plurality of fields of the beam being adjustable with respect to the rendering of the treatment target;

identifying a subset of fields of the plurality of fields that satisfy a criterion based on the rendering of the treatment target and the rendering of the plurality of fields of the beam, the criterion being an amount of a Bragg peak outside of a patient's body; and storing, in memory of the computer system, values of the angles of the fields in the subset.

10. The non-transitory computer-readable storage medium of claim 9, wherein the rendering of the plurality of fields indicates a location of a respective Bragg peak in each of the fields.

11. The non-transitory computer-readable storage medium of claim 9, wherein the rendering of the plurality of fields shows a range of each field of the plurality of fields and coverage of each field relative to the treatment target.

12. The non-transitory computer-readable storage medium of claim 11, wherein the range of each field of the plurality of fields is determined using a respective value of radiological thickness for each field of the plurality of fields.

13. The non-transitory computer-readable storage medium of claim 9, wherein the rendering of the plurality of fields of the beam shows a width of each field of the plurality of fields.

14. The non-transitory computer-readable storage medium of claim 9, wherein a field of the plurality of fields satisfies the criterion and is included in the subset of fields when a threshold amount of a Bragg peak of the field is outside the patient's body.

15. A computer-implemented method used for radiation treatment planning, the method comprising:

accessing information comprising a location of an isocenter based on a location of a treatment target in a patient;

accessing information comprising a value of beam energy for a beam of radiation having a path that is toward the isocenter;

accessing information comprising a value of radiological thickness associated with the path;

determining, using the value of radiological thickness and the value of beam energy, a range of a field of the beam of radiation along the path and relative to the treatment target and the patient;

determining whether the range of the field of the beam satisfies a criterion, the criterion being an amount of a Bragg peak outside of a patient's body;

outputting a treatment plan including the range of the field of the beam that satisfies the criterion; and displaying, on a display device, a graphical user interface (GUI) comprising a rendering of the treatment target and a rendering of the range of the field of the beam relative to the treatment target and the patient, the rendering of the range of the field of the beam being adjustable with respect to the rendering of the treatment target to determine whether the range of the field of the beam satisfies the criterion.

16. The computer-implemented method of claim 15, wherein the rendering of the range of the field of the beam also indicates a location in the field of the Bragg peak.

17. The computer-implemented method of claim 15, wherein the rendering of the range of the field of the beam also shows width of the field relative to the treatment target.

18. The computer-implemented method of claim 15, further comprising:

when the criterion is satisfied, including a value of an angle of the beam in the treatment plan.

19. The computer-implemented method of claim 18, wherein the criterion is satisfied when a threshold amount of the Bragg peak is outside the patient's body.

* * * * *